_(12)_ United States Patent
Tonani et al.

(10) Patent No.: US 7,786,048 B2
(45) Date of Patent: Aug. 31, 2010

(54) CONDENSED HETEROCYCLIC PYRAZOLE DERIVATIVES AS KINASE INHIBITORS

(75) Inventors: Roberto Tonani, Novate (IT); Simona Bindi, Milan (IT); Daniele Fancelli, Milan (IT); Valeria Pittala', Catania (IT); Mario Varasi, Milan (IT)

(73) Assignee: Pfizer Italia S.r.l., Rome (IT)

( * ) Notice: Subject to any disclaimer, the term of this patent is extended or adjusted under 35 U.S.C. 154(b) by 0 days.

(21) Appl. No.: 12/472,513

(22) Filed: May 27, 2009

(65) Prior Publication Data

US 2009/0233813 A1 Sep. 17, 2009

Related U.S. Application Data

(63) Continuation of application No. 10/522,250, filed as application No. PCT/EP03/07531 on Jul. 11, 2003, now Pat. No. 7,541,378.

(60) Provisional application No. 60/398,121, filed on Jul. 25, 2002.

(51) Int. Cl.
C40B 40/14 (2006.01)
C40B 40/04 (2006.01)
(52) U.S. Cl. .......................................... 506/20; 506/15
(58) Field of Classification Search ................... 506/15, 506/20
See application file for complete search history.

(56) References Cited

U.S. PATENT DOCUMENTS

2005/0187209 A1 8/2005 Fancelli et al.

OTHER PUBLICATIONS

Elnagdi M.H. et al., "The Reaction of Phenacyl Malononitrile with Hydrazines: Synthesis of New Pyridazinones and Pyrazolo[1,5-α] Pyrimidines", _Gazzetta Chimica Italiana_ 127:791-794 (1997), XP009018422.
Sherif S.M. et al., "Syntheses with Heterocyclicβ—Enaminonitriles: An Expeditious Synthetic Approach to Polyfunctionally Substituted 5-Phenyl-Suflonylthiophenes and their Fused Derivatives", _Monatshefte für Chemie_ 128:687-696 (1997), XP009018423.
Abdel Fattah Ali Harb, "Nitriles in Heterocyclic Synthesis: Novel Routus to Cyclopentenothienopyridines, Cyclopentenothieno-Pyrimidenes and Cyclopentenopyrrolopyrazoles", _Egyptian Journal of Pharmaceutical Sciences_ 33(1-2):283-292 (1992).
Abdelrazek F.M. et al., "Nitriles in Heterocyclic Synthesis. A Novel Synthesis of 4-Phenacylpyrazole and Pyrrolo[2,3-c]Pyrazole", _Synthesis_ 74-75 (1986), XP-001155261.

_Primary Examiner_—Kamal A Saeed
_Assistant Examiner_—Kristin Bianchi
(74) _Attorney, Agent, or Firm_—Scully, Scott, Murphy & Presser, P.C.

(57) ABSTRACT

Bicyclo-pyrazole compound of formula (I) and pharmaceutically acceptable salts thereof, as defined in the specification, processes for their preparation, combinatorial libraries comprising a plurality of them and pharmaceutical compositions thereof, are herewith disclosed: the compounds of the invention are useful, in therapy, as protein kinase inhibitors, for instance in the treatment of cancer.

4 Claims, No Drawings

CONDENSED HETEROCYCLIC PYRAZOLE DERIVATIVES AS KINASE INHIBITORS

CROSS REFERENCE TO RELATED APPLICATION

This application is a continuation of application Ser. No. 10/522,250 filed on Sep. 19, 2005, which is a 371 of PCT/EP2003/007531 filed on Jul. 11, 2003, which claims the benefit of U.S. Provisional Application No. 60/398,121 filed on Jul. 25, 2002.

The present invention relates to novel condensed heterocyclic pyrazole derivatives, to a process for their preparation, to pharmaceutical compositions comprising them and to their use as therapeutic agents, in particular in the treatment of diseases linked to disregulated protein kinases.

The malfunctioning of protein kinases (Pks) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis. PKs are also implicated in inflammatory conditions and in the multiplication of viruses and parasites. PKs may also play a major role in the pathogenesis and development of neurodegenerative disorders.

For a general reference to PKs malfunctioning or disregulation see, for instance, Current Opinion in Chemical Biology 1999, 3, 459-465.

Accordingly, there is the need in therapy of compounds active in modulating disregulated protein kinases, and in particular endowed with protein kinase inhibiting activity.

The present inventors have now discovered that novel condensed heterocyclic pyrazole derivatives, according to the present invention, are endowed with modulating disregulated protein kinase activity, and are thus useful in therapy in the treatment of diseases associated with disregulated protein kinases.

The present invention, as first object, provides a bicyclopyrazole compound of formula (I):

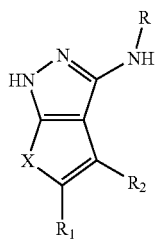

(I)

wherein
X is NR', O, S, SO or $SO_2$;
each of R and $R_1$, being the same or different, is independently a hydrogen atom or an optionally substituted group selected from R', —COR', —COOR', —CONHR', —CONR'R", —$SO_2$R', —$SO_2$NHR' or —$SO_2$NR'R"; wherein each of R' and R", being the same or different, is independently selected from hydrogen or an optionally further substituted straight or branched $C_1$-$C_6$ alkyl, heterocyclyl, aryl or aryl-$C_1$-$C_6$ alkyl group;

$R_2$ is an optionally substituted group selected from R', —$CH_2$OR' and OR', wherein R' is as above defined; and the pharmaceutically acceptable salts thereof.

The compounds of formula (I), object of the present invention, may have asymmetric carbon atoms and may therefore exist both as individual optical isomers and as racemic admixtures thereof. Accordingly, all of the possible single isomers, including optical and geometrical isomers, of the compounds of formula (I) and admixtures thereof are also object of the invention. The present invention comprises also the metabolites and the pharmaceutically acceptable bio-precursors, otherwise referred to as pro-drugs, of the compounds of formula (I).

As it will be appreciated, the unsubstituted nitrogen atom in the condensed pyrazole ring of the compounds of the invention can rapidly equilibrate, in solution, as admixture of both tautomers:

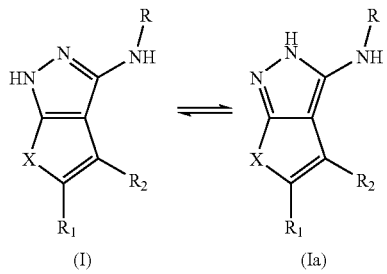

(I)          (Ia)

Accordingly, where only one tautomer (I) or (Ia) is herein indicated for the compounds of the invention, the other one and any mixture thereof, are also within the scope of the present invention, unless specifically noted otherwise.

As used herein and unless other specified, the term straight or branched $C_1$-$C_6$ alkyl, either as such or as a moiety in an aryl-alkyl group, is meant a group chosen for instance from methyl, ethyl, n.propyl, isopropyl, n.butyl, isobutyl, sec-butyl, tert-butyl, n.pentyl, n.hexyl and the like. Preferably it is a straight or branched $C_1$-$C_4$ alkyl, e.g. methyl, ethyl, n.propyl, isopropyl, n.butyl, isobutyl, sec-butyl and tert-butyl.

An aryl group, either as such or as aryl-alkyl group, is for instance a mono-, bi- or poly-either carbocyclic as well as heterocyclic hydrocarbon, with preferably from 1 to 4 ring moieties, either fused or linked to each other by single bonds, wherein at least one of the carbocyclic or heterocyclic rings is aromatic.

Non limiting examples of aryl groups are phenyl, indanyl, biphenyl, α- or, β-naphthyl, fluorenyl, 9,10-dihydroanthracenyl, pyridyl, pyrazinyl pyrimidinyl, pyridazinyl, indolyl, imidazolyl, imidazopyridyl, 1,2-methylenedioxyphenyl, thiazolyl, isothiazolyl, pyrrolyl, pyrrolyl-phenyl, furyl, phenyl-furyl, benzotetrahydrofuranyl, oxazolyl, isoxazolyl, pyrazolyl, chromenyl, thienyl, benzothienyl isoindolinyl, benzoimidazolyl, tetrazolyl, tetrazolylphenyl, pyrrolidinyl-tetrazolyl, isoindolinyl-phenyl, quinolinyl, isoquinolinyl, 2,6-diphenyl-pyridyl, quinoxalinyl, pyrazinyl, phenyl-quinolinyl, benzofurazanyl, 1,2,3-triazolyl, 1-phenyl-1,2,3-triazolyl, and the like.

Accordingly, the term aryl group may also refer to aromatic carbocyclic or heterocyclic rings, further fused or linked to non aromatic heterocyclic rings, typically 5 to 7 membered heterocycles.

With the term 5 to 7 membered heterocycle, hence encompassing aromatic heterocycles also referred to as aryl groups, we also intend a saturated or partially unsaturated 5 to 7 membered carbocycle, wherein one or more, e.g. 1 to 3 carbon atoms, are replaced by heteroatoms such as nitrogen, oxygen and sulphur.

Examples of 5 to 7 membered heterocycles, optionally benzocondensed or further substituted, are 1,3-dioxolane, pyran, pyrrolidine, pyrroline, imidazolidine, pyrazolidine, pyrazoline, piperidine, piperazine, morpholine, tetrahydrofuran, azabicyclononane and the like.

According to the above meanings provided to R, $R_1$, $R_2$ R' and R", any of the above groups may be further optionally substituted, in any of their free positions, by one or more groups, for instance 1 to 6 groups, selected from: halogen, nitro, oxo groups (=O), carboxy, cyano, alkyl, perfluorinated alkyl alkenyl, alkynyl, cycloalkyl, aryl, heterocyclyl, amino groups and derivatives thereof such as, for instance, alkylamino, dialkylamino, arylamino, diarylamino, ureido, alkylureido or arylureido; carbonylamino groups and derivatives thereof such as, for instance, formylamino, alkylcarbonylamino, alkenylcarbonylamino, arylcarbonylamino, alkoxycarbonylamino, sulfonamido, alkylsulfonamido and arylsulfonamido, hydroxy groups and derivatives thereof such as, for instance, alkoxy, aryloxy, alkylcarbonyloxy, arylcarbonyloxy, cycloalkenyloxy or alkylideneaminooxy, carbonyl groups and derivatives thereof such as, for instance, alkylcarbonyl, arylcarbonyl, alkoxycarbonyl, aryloxycarbonyl, cycloalkyloxycarbonyl, aminocarbonyl, alkylaminocarbonyl, dialkylaminocarbonyl; sulfurated derivatives such as, for instance, alkylthio, arylthio, alkylsulphonyl, arylsulphonyl, alkylsulphinyl, arylsulphinyl, arylsulphonyloxy, aminosulfonyl, alkylaminosulphonyl or dialkylaminosulphonyl. In their turn, whenever appropriate, each of the above substituents may be further substituted by one or more of the aforementioned groups.

A halogen atom is for instance fluorine, chlorine, bromine or iodine.

Any alkyl, alkenyl, alkynyl or alkoxy group can be either a branched or straight moiety.

An alkyl group or moiety is, for instance, a $C_1$-$C_6$ alkyl group, in particular a $C_1$-$C_4$ alkyl group as exemplified above.

An alkoxy group is for instance a $C_{1-6}$ alkoxy group, in particular a $C_1$-$C_4$ alkoxy group such as methoxy, ethoxy, propoxy, isopropoxy, butoxy, sec-butoxy or tert-butoxy.

An alkenyl or alkynyl group is for instance a $C_2$-$C_6$ alkenyl or alkynyl chain, in particular a $C_2$-$C_4$ alkenyl or alkynyl chain, preferably a vinyl, allyl or ethynyl group, respectively.

An aryl or heterocyclyl group or moiety is, for instance, an aryl or heterocyclyl group or moiety, as defined above.

A cycloalkyl group is, for instance, a $C_3$-$C_6$ cycloalkyl group such as cyclopropyl, cyclobutyl, cyclopentyl or cyclohexyl.

Pharmaceutically acceptable salts of the compounds of formula (I) are the acid addition salts with inorganic or organic acids, e.g. nitric, hydrochloric, hydrobromic, sulphuric, perchloric, phosphoric, acetic, trifluoroacetic, propionic, glycolic, lactic, oxalic, malonic, malic, maleic, tartaric, citric, benzoic, cinnamic, mandelic, methanesulphonic, isethionic and salicylic acid, as well as the salts with inorganic or organic bases, e.g. alkali or alkaline earth metals, especially sodium, potassium, calcium or magnesium hydroxides, carbonates or bicarbonates, acyclic or cyclic amines, preferably methylamine, ethylamine, diethylamine, triethylamine or piperidine.

Preferred compounds of the invention are the compounds of formula (I) wherein X is S or O; R is —CONHR'; $R_1$ is —COR', —CONHR', —CONR'R", —SO$_2$NHR' or —SO$_2$NR'R", wherein each of R' and R", being the same or different, is selected from hydrogen or an optionally substituted straight or branched $C_1$-$C_6$ alkyl, aryl and aryl-$C_1$-$C_6$ alkyl group; $R_2$ is hydrogen; and the pharmaceutically acceptable salts thereof.

Even more preferred, are the compounds of the invention of formula (I) wherein X is S; R is —CONHR'; $R_1$ is —CONHR' or —CONR'R", wherein each of R' and R", being the same or different, is selected from hydrogen or an optionally substituted straight or branched $C_1$-$C_6$ alkyl, aryl or aryl-$C_1$-$C_6$ alkyl group; $R_2$ is hydrogen; and the pharmaceutically acceptable salt thereof.

For a general reference to any specific compound of formula (I) of the invention, optionally in the form of a pharmaceutically acceptable salt, see the experimental section and claims.

As formerly indicated, as an additional object of the invention herewith provided are the compounds of formula (I), or the pharmaceutically acceptable salts thereof, for use as a medicament.

In addition, the present invention also provides the use of the compounds of formula (I), or the pharmaceutically acceptable salts thereof, in the manufacture of a medicament for treating a patient suffering from a disease caused by and/or associated with an altered (disregulated) protein kinase activity.

The present invention thus provides a method for treating a mammal, including humans, suffering from a disease caused by and/or associated with an altered (disregulated) protein kinase activity, which comprises administering to said mammal in need thereof a therapeutically effective amount of a bicyclo-pyrazole compound of formula (I):

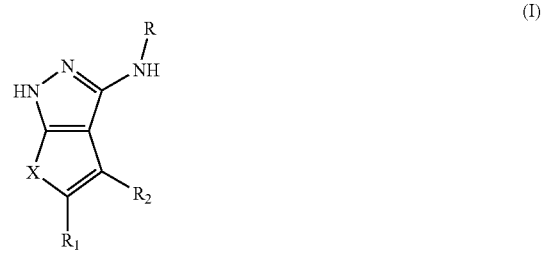

(I)

wherein
X is NR', O, S, SO or SO$_2$;
each of R and $R_1$, being the same or different, is independently a hydrogen atom or an optionally substituted group selected from R', —COR', —COOR', —CONHR', CONR'R", —SO$_2$R', —SO$_2$NR' or —SO$_2$NR'R"; wherein each of R' and R", being the same or different, is independently selected from hydrogen or an optionally further substituted straight or branched $C_1$-$C_6$ alkyl, heterocyclyl, aryl or aryl-$C_{1-6}$ alkyl group;
$R_2$ is an optionally substituted group selected from R', —CH$_2$OR' and OR', wherein R' is as above defined; and the pharmaceutically acceptable salts thereof.

In a preferred embodiment, the disease caused by and/or associated with an altered (disregulated) protein kinase activity is selected from the group consisting of cancer, cell proliferative disorders, Alzheimer's disease, viral infections, autoimmuno diseases and neurodegenerative disorders.

Specific preferred types of cancer that may be treated include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratoxanthomas, thyroid follicular cancer and Kaposi's sarcoma.

In another preferred embodiment of the method for treating a mammal described above, the cell proliferative disorder is selected from the group consisting of benign prostate hyperplasia, familial adenomatosis polyposis, neuro-fibromatosis, psoriasis, vascular smooth cell proliferation associated with atherosclerosis, pulmonary fibrosis, arthritis glomerulonephritis and post-surgical stenosis and restenosis.

In addition, the method for treating a mammal object of the present invention also provides tumor angiogenesis and metastasis inhibition.

A further object of the invention is also represented by the process for preparing the compounds of formula (I) of the invention, and the pharmaceutically acceptable salts thereof, which process comprises:

a) reacting a compound of formula (II)

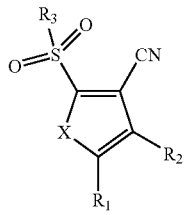

(II)

wherein $R_1$, $R_2$ and X are as defined above and $R_3$ is a lower alkyl group, with hydrazine or a hydrazine salt, so as to obtain a compound of formula (I) wherein R is hydrogen and $R_1$, $R_2$ and X are as defined above; and, if desired, b) converting the thus obtained compound of formula (I) into another compound of formula (I) wherein R is other than a hydrogen atom; and/or, if desired, converting the compound of formula (I) into a pharmaceutically acceptable salt thereof and/or the salt of a compound of formula (I) into a free compound thereof.

The above process is an analogy process, which can be carried out according to known methods in the art.

From the above, it is clear to the person skilled in the art that if a compound of formula (I), prepared according to the above process, is obtained as an admixture of isomers, their separation into the single isomers of formula (I), carried out according to conventional techniques, is still within the scope of the present invention.

Likewise, salification of a compound of formula (I) or conversion of a corresponding salt thereof into the free compound (I), according to step (b) of the process, can be easily carried out according to well-known methods in the art.

According to step a) of the process, the reaction between a compound of formula (II) and hydrazine or a hydrazine salt, for instance hydrazine dihydrochloride or hydrazine sulphate or acetate, can be carried out in the presence of catalytic amounts of an acid such as hydrochloric, acetic or sulphuric acid, or in the presence of catalytic amounts of a Lewis acid such as boron trifluoride dimethyl etherate, or even in the presence of catalytic amounts of a strong base such us sodium methoxide.

The reaction is carried out in a suitable solvent such as, for instance, N,N'-dimethylformamide, tetrahydrofuran, 1,4-dioxane, acetonitrile, water, methanol or ethanol, at a temperature ranging from about room temperature to reflux and for a time varying from about 30 minutes to about 18 hours.

According to a preferred embodiment, within the compounds of formula (II), $R_3$ is a straight or branched lower alkyl group, for instance a $C_1$-$C_6$ alkyl group and, even more preferably, a $C_1$-$C_4$ alkyl group.

Preferably, step a) is carried out by reaction of a compound of formula (II) and hydrazine hydrate in ethanol, at a temperature ranging from room temperature and refluxing temperature followed by cyclization of the intermediate 2-hydrazinothiophene thus obtained. Cyclization is carried out at a temperature ranging from about 15° C. to about 50° C. in methanol or ethanol, and in the presence of catalytic amounts of a mineral acid such as hydrochloric or sulphuric acid.

The thus obtained bicyclo-pyrazoles of formula (I) and wherein R is hydrogen, as per step a), can be easily converted into a variety of derivatives of formula (I) having R other than a hydrogen atom, and/or into salts thereof.

As set forth in step (b), any of these conversions may occur according to conventional techniques, by properly reacting the amino derivative (I) with alkylating, acylating, sulfonylating agents and the like.

In this respect it is worth noting that optional by-products, for instance originating by the above reactions also occurring at the nitrogen pyrazole atom, may be obtained. As such, a subsequent step to isolate the desired compound of formula (I) is then required and carried out according to the methods known in the art.

Optionally, compounds obtained by reacting the amino derivative (I) with acylating agents and wherein acylation occurred at both the amino group and the nitrogen pyrazole atom, can be easily converted into the corresponding compounds of formula (I) by selective hydrolysis of the acyl group at the pyrazole nitrogen atom.

Likewise, a compound of formula (I) obtained according to step a) above, can be first reacted with an opportune acylating agent to protect the pyrazole nitrogen atom, then reacted as per step b), and finally de-protected at the pyrazole nitrogen atom.

Alternatively, a compound of formula (I) being obtained according to step a), may be first supported onto a suitable resin and, then reacted as per step b) above followed by resin cleavage.

Therefore, object of the present invention is also a process for preparing a compound of formula (I) and the pharmaceutically acceptable salts thereof, which process comprises:

a) reacting a compound of formula (II) as above defined with hydrazine or a hydrazine salt so as to obtain a compound of formula (I) wherein R is a hydrogen atom and $R_1$, $R_2$ and X are as defined above;

a') reacting the thus obtained compound of formula (I) with an alkyl chlorocarbonate of formula (III)

$$R_3\text{—O—CO—Cl} \quad \text{(III)}$$

wherein $R_3$ is a lower allyl group, so as to obtain a compound of formula (IV) being protected at the heterocyclic pyrazole nitrogen atom:

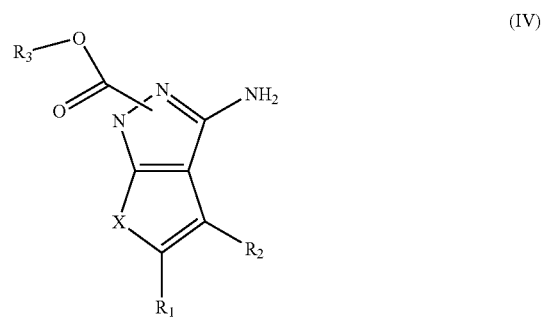

(IV)

b) converting the thus obtained compound of formula (IV) into a compound of formula (V)

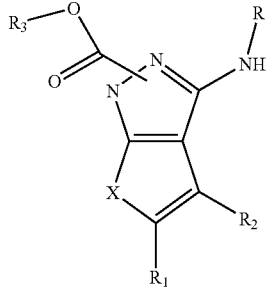

(V)

wherein R, being as defined above, is other than a hydrogen atom and X, $R_1$, $R_2$ and $R_3$ are as defined above; and c) cleaving the protecting group under alkaline conditions so as to obtain the desired compound of formula (I) and, if desired, converting the thus obtained compound of formula (I) into another compound of formula (I); and/or, if desired, converting the compound of formula (I) into a pharmaceutically acceptable salt thereof and/or the salt thereof into a free compound of formula (I).

In step a'), the reaction between the alkyl chlorocarbonate of formula (III) and the compound of formula (I), as therein defined, can be carried out in a suitable solvent such as, tetrahydrofuran, dichloromethane, chloroform, acetonitrile, toluene or a mixture thereof, at a temperature ranging from about −5° C. to about 35° C. and for a time varying from about 30 minutes to about 72 hours, in the presence of an opportune proton scavenger such as triethylamine or diisopropylethylamine.

After having carried out the conversion of a compound of formula (IV) into a compound of formula (V), as described below, the subsequent de-protection, in step c), is carried out under alkaline conditions by working according to conventional techniques, for instance by treatment with aqueous sodium or potassium hydroxide in the presence of a suitable co-solvent such as methanol, ethanol, dimethylformamide, 1,4-dioxane, or by treatment with a tertiary amine such as triethylamine or disopropylethylamine using an alcohol like methanol or ethanol as the solvent.

Deprotection occurs at a temperature ranging from about 18° C. to refluxing temperature of the solvent, for a time varying from about 30 minutes to about 72 hours.

A further object of the invention is also a process for preparing a compound of formula (I) and the pharmaceutically acceptable salts thereof, in which X, $R_1$ and $R_2$ are as defined above and R is an optionally substituted group selected from —COR' or —COOR', which process comprises:

a") reacting a compound of formula (I) as obtained in the above step (a) and wherein R is a hydrogen atom with an excess of a chlorocarbonate or an acyl chloride derivative of formula (IIIa) or (IIIb), respectively:

   (IIIa)

   (IIIb)

wherein R' is as above defined, so as to obtain a compound of formula (Va) or (Vb), respectively

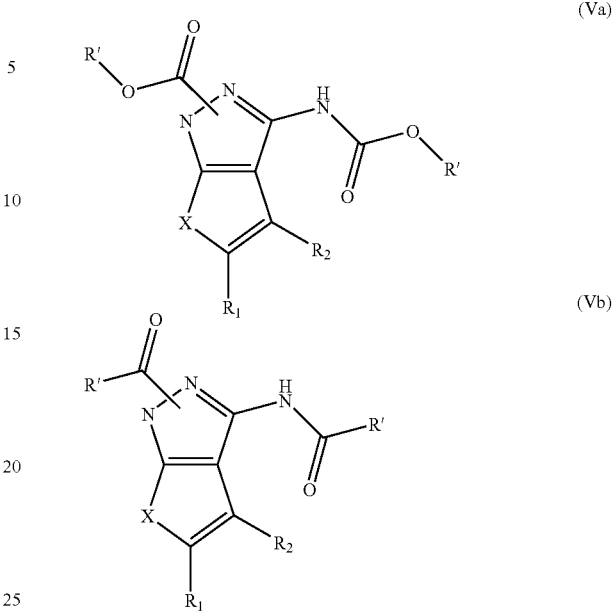

c') cleaving under alkaline conditions the compound of formula (Va) or (Vb) so as to eliminate the protecting group at the pyrazole nitrogen atom and thus obtaining the desired compound of formula (I) and, if desired, converting the thus obtained compound of formula (I) into another compound of formula (I); and/or, if desired, converting the compound of formula (I) into a pharmaceutically acceptable salt thereof and/or the salt thereof into a free compound of formula (I).

In step a"), the reaction between the compound of formula (IIIa) or (IIIb) with the compound of formula (I), as therein defined, can be carried out in a suitable solvent such as, tetrahydrofuran, dichloromethane, chloroform, acetonitrile, toluene or a mixture thereof, at a temperature ranging from about −5° C. to about 35° C. and for a time varying from about 30 minutes to about 72 hours, in the presence of an opportune proton scavenger such as triethylamine or diisopropylethylamine.

The subsequent selective hydrolysis of the acyl group at the pyrazole nitrogen atom, in step c'), is carried out under alkaline conditions by working according to conventional techniques, as formerly reported.

According to a further aspect of the process, a compound of formula (I) being obtained as per step a) above, is first supported onto a suitable resin and, then, reacted as per step b). Therefore an additional object of the invention is also a process for preparing a compound of formula (I) and the pharmaceutically acceptable salts, which process comprises:

a''') reacting a compound of formula (I) wherein R is a hydrogen atom and $R_1$, $R_2$ and X are as above defined; with an isocyanate polystyrenic resin of formula (VI)

(VI)

so as to obtain a polystyrenemethyl urea; of formula (VII)

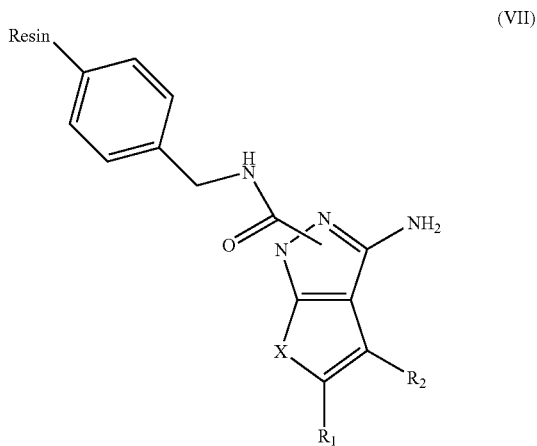
(VII)

b) converting the thus obtained compound of formula (VII) into a compound of formula (VIII)

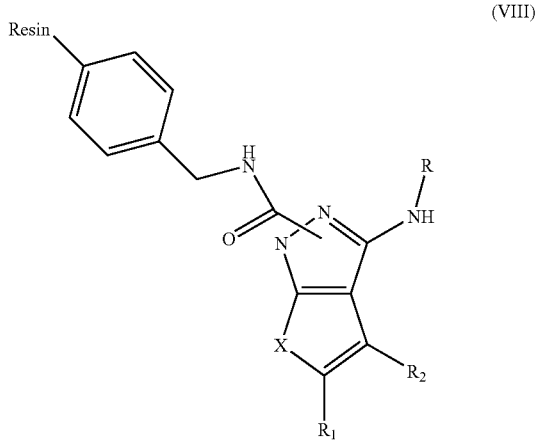
(VIII)

wherein R, being as defined above, is other than a hydrogen atom; and c″) cleaving under alkaline conditions the compound of formula (VIII) so as to eliminate the resin and thus obtaining the desired compound of formula (I) and, if desired, converting the thus obtained compound of formula (I) into another compound of formula (I); and/or, if desired, converting the compound of formula (I) into a pharmaceutically acceptable salt thereof and/or the salt thereof into a free compound of formula (I).

In step a′″), the reaction between the isocyanatomethyl polystyrenic resin of formula (VI) and the compound of formula (I), as therein defined, can be carried out in a suitable solvent such as, N,N-dimethylformamide, dichloromethane, chloroform, acetonitrile, toluene or a mixture thereof, at a temperature ranging from about 5° C. to about 35° C. and for a time varying from about 30 minutes to about 72 hours.

After having carried out the conversion of a compound of formula (VII) into a compound of formula (VIII), as formerly described, the subsequent cleavage of the resin, in step c″), is carried out under alkaline conditions by working according to conventional techniques. As an example, aqueous sodium or potassium hydroxides in the presence of a suitable co-solvent such as methanol, ethanol, dimethylformamide, 1,4-dioxane, or acetonitrile can be employed.

The conversion of a compound of formula (VII) into a compound of formula (VIII) can be carried out under mild operative conditions, at temperatures varying from about 5° C. to about 60° C. and for a time varying from about 2 hours to about 7 days.

As far as step b) of the process is concerned, the optional conversion of a compound of formula (I) or, more preferably, of formulae (IV) or (VII), into the corresponding derivatives of formula (I), (V) or (VIII), respectively, and having R other than hydrogen, can be carried according to conventional techniques known in the art to alkylate, acylate or sulfonylate amino groups.

In particular, a compound of formula (I) wherein R, being other than hydrogen, is selected from: R', —COR', —COOR', —SO$_2$R', —SO$_2$NHR' and —SO$_2$NR'R", wherein R' and R" have the values as given in formula (I) above; and R$_1$ and R$_2$ are as defined above, may be prepared by reacting a compound of formula (I), wherein R is hydrogen, with a corresponding compound of formula (IX)

R—Y (IX)

wherein R has the above reported meanings other than hydrogen, and Y is a suitable leaving group, preferably chlorine or bromine.

The above conditions apply, by analogy, either to the conversion of a compound of formula (IV) into a compound of formula (V), through reaction with a derivative o formula (IX), as well as to the conversion of a compound of formula (VII) to the compound of formula (VIII), through reaction with a derivative o formula (IX).

The above reaction can be carried out according to conventional procedures known in the art for acylating, sulfonylating or alkylating amino groups, for instance in the presence of a tertiary base, such as triethylamine, N,N-diisopropylethylamine or pyridine, in a suitable solvent such as toluene, dichloromethane, chloroform, diethyl ether, tetrahydrofuran, acetonitrile, or N,N-dimethylformamide, at a temperature ranging from about −10° C. to reflux and for a time varying from about 30 minutes to about 96 hours. From the foregoing, it is clear to the person skilled in the art that the preparation of the compounds of formula (I) having R equal to —SO$_2$NR'R" can be actually performed as above described or, alternatively, by properly reacting a compound of formula (I) or (V) having R equal to —SO$_2$NHR' with any suitable alkylating moiety, according to well known methodologies for preparing di-substituted sulfonamides.

A compound of formula (I) wherein R is a —CONHR' group, R' has the above reported meanings other than hydrogen, X, R$_1$ and R$_2$ are as above defined, may be prepared by reacting a compound of formula (I) having R equal to hydrogen, with a compound of formula (X)

R'NCO (X)

wherein R' is as above defined other than hydrogen.

The above conditions apply, by analogy, either to the conversion of a compound of formula (IV) into a compound of formula (V), through reaction with a derivative o formula (X), as well as to the conversion of a compound of formula (VII) to the compound of formula (VIII), through reaction with a derivative o formula (X). Compounds of formula (I), (V) or (VIII) wherein R is a —CONHR' group may be optionally further reacted with a compound of formula (XI)

R"—Y (XI)

wherein R" is as above defined other than hydrogen and Y is a suitable leaving group, preferably chlorine or bromine, so as to obtain the corresponding compounds of formulae (I), (V) or (VIII) wherein R is —CONR'R", being R' and R" other than hydrogen atoms. The reaction between the above compounds (I), (IV) or (VII) with a compound of formula (X) can be carried out in the presence of a tertiary base, such as triethylamine, N,N-diisopropylethylamine or pyridine, in a suitable solvent, such as toluene, dichloromethane, chloroform, diethyl ether, tetrahydrofuran, acetonitrile, or N,N-dimethylformamide, at a temperature ranging from about −10° C. to reflux. The reaction time may vary from about 30 minutes to about 72 hours.

The optional subsequent conversion of a compound of formula (I), (V) or (VIII) having R equal to —CONHR' into a corresponding derivative having R equal to —CONR'R" is carried out according to conventional methods used to prepare di-substituted ureido derivatives.

A compound of formula (I) or (V) wherein R is a —CONR'R" group, R' and R" have the above reported meanings other than hydrogen, X, $R_1$ and $R_2$ are as above defined, may be prepared by reacting a compound of formula (I) or (IV) having R equal to hydrogen, with 4-nitrophenylchloroformate and subsequently with a compound of formula (XII)

wherein R' and R", are as defined above other than hydrogen.

The reaction is carried out according to conventional methods used to prepare di-substituted ureido derivatives.

Analogously, a compound of formula (VIII) wherein R is a —CONR'R" group, R' and R" have the above reported meanings other than hydrogen, X, $R_1$ and $R_2$ are as above defined, may be prepared by reacting a compound of formula (VII), having R equal to hydrogen with 4-nitrophenylchloroformate and, subsequently, with a compound of formula (XII) as defined above.

Alternatively, a compound of formula (I), or a compound of formula (IV), having R equal to hydrogen, may be reacted under reductive conditions with a compound of formula (XIII)

wherein R', being as defined above is other than hydrogen, so as to obtain a corresponding compound of formula (I) or (V) wherein R is a R'CH$_2$— group and R' being as defined above is other than hydrogen.

Analogously, a compound of formula (VII) heaving R equal to hydrogen may be reacted under reductive conditions with a compound of formula (XIII) as defined above, so as to obtain a corresponding compound of formula (VIII) wherein R is a R'CH$_2$— group and R' being as defined above is other than hydrogen.

The reaction is carried out in a suitable solvent such as, for instance, N,N-dimethylformamide, N,N-dimethylacetamide, chloroform, dichloromethane, tetrahydrofuran, or acetonitrile, optionally in the presence of acetic acid, ethanol or methanol as co-solvents, at a temperature ranging from about −10° C. to reflux and for a time varying from about 30 minutes to about 4 days.

Conventional reducing agents in the reaction medium are, for instance, sodium boron hydride, sodium triacethoxy boron hydride, and the like.

From the foregoing, it is clear to the person skilled in the art than any of the above compounds of formula (I), (IV), (V), (VII) and (VIII) may be conveniently converted into other derivatives (I), (IV), (V), (VII) or (VIII) also by properly reacting functional groups other than the R group, extensively described above, according to conventional synthetic organic methods.

In a further example, the compounds of formula (I) or (VIII) wherein $R_1$ is —COOMe can be hydrolized to the corresponding compounds of formula (I) or (VIII) wherein $R_1$ is —COOH, by treatment with a suitable base, for instance sodium or potassium hydroxide, according to conventional synthetic organic methods.

Any of the above compounds of formula (I) or (VIII) and where $R_1$ is a —COOH group can be easily converted into other derivatives (I) or (VIII) by properly reacting the carboxylic group according to conventional synthetic organic methods.

In particular, a compound of formula (I) or (VIII) wherein $R_1$ is a —CONR'R" group, R' and R" have the above reported meanings other than hydrogen, R is as above defined other than hydrogen, and X and $R_2$ are as above defined, may be prepared by reacting a corresponding compound of formula (I) or (VIII), wherein $R_1$ is a —COOH group, with a condensing agent and, subsequently, with a compound of formula (XII)

wherein R' and R", are as defined above.

The reaction is carried out according to conventional methods used to prepare amides. Likewise, a compound of formula (I) or (VIII) wherein $R_1$ is —COR', R' has the above reported meanings, R is other than hydrogen, and $R_2$ and X are as above defined, may be prepared by reacting a corresponding compound of formula (I) or (VIII), wherein $R_1$ is a Weinreb amido —CONCH$_3$OCH$_3$ group with a compound of formula (XIV)

wherein R' is as defined above other than hydrogen.

The reaction is carried out according to conventional methods used to prepare ketones. As an example, the reaction between the above compounds (I) or (VIII) with a compound of formula (XIV) can be carried out in a suitable solvent, such as tetrahydrofuran, toluene, diethyl ether, hexane, at a temperature ranging from about −78° C. to about 10° C. and for a time varying from about 10 minutes to about 72 hours. A compound of formula (I) or (V) wherein $R_1$ is a Weinreb amido CONCH$_3$OCH$_3$ group can be obtained by known methods.

Alternatively a compound of formula (I) or (VIII) wherein $R_1$ is a —COOR' group, R' has the above reported meanings other than hydrogen, R is other than hydrogen, and $R_2$ and X are as above defined, may be prepared by reacting a corresponding compound of formula (I) or (VIII), wherein $R_1$ is a —COOH group with a compound of formula (XV)

wherein R' is as defined above other than hydrogen.

The reaction is carried out according to conventional methods used to prepare esters. Likewise, the preparation of the compounds of formula (V) or (VIII) having $R_1$ equal to —SO$_2$NR'R" can be actually performed as described below or, alternatively, by properly reacting a compound of formula (V) or (VIII) having $R_1$ equal to —SO$_2$NHR' with any suitable alkylating moiety, according to well known methodologies for preparing di-substituted sulfonamides.

From the foregoing, it is clear to the person skilled in the art than any of the above compounds of formula (I) and (VIII) may be conveniently converted into other derivatives (I) or (VIII) also by properly reacting functional groups other than the R and R₁ groups, extensively described above, according to conventional synthetic organic methods.

As an example, a compound of formula (I) or (VIII) wherein X is SO, R is other than hydrogen, and R₁ and R₂ are as defined above, may be conveniently prepared by starting from a corresponding compound of formula (I) or (VIII) wherein X is S with an oxidizing agent according to conventional synthetic organic methods. The reaction can be carried out in the presence of an oxidizing agent such as, for instance, boron-trifluoride diethyl etherate in the presence of MCPBA, hydrogen peroxide in the presence of TFA and the like, in a suitable solvent such as dichloromethane, water, methanol, ethanol at a temperature ranging from about –10° C. to reflux and for a time varying from about 30 minutes to about 48 hours.

In a further example, a compound of formula (I) or (VIII), wherein X is SO₂, R is other than hydrogen, and R₁ and R₂ are as defined above, may be conveniently prepared by starting from a corresponding compound of formula (I) or (VIII) wherein X is S, with an oxidizing agent according to conventional synthetic organic methods. As an example, the reaction can be carried out in the presence of an oxidizing agent, such as, for instance, MCPBA, dimethyldioxirane, oxone, Mg monoperoxyphthalate, in a suitable solvent such as, dichloromethane, chloroform, acetone, acetonitrile, water, methanol, ethanol, at a temperature ranging from about –10° C. to reflux and for a time varying from about 30 minutes to about 48 hours.

In a further example, a compound of formula (V) or (VIII) wherein X is NR', R' and R are other than hydrogen atoms, and R₁ and R₂ are as defined above, may be conveniently prepared by staring from a corresponding compound of formula (V) or (VIII) wherein X is NH, through reaction with a compound of formula (XVI)

R'—Y  (XVI)

wherein R', being as defined above, is other than hydrogen and Y is a suitable leaving group, preferably chlorine or bromine. This latter reaction can be carried out in the presence of a base such as sodium hydride, tBuOK, potassium carbonate, potassium hydroxide and the like, in a suitable solvent such as toluene, dichloromethane, chloroform, diethyl ether, tetrahydrofuran, acetonitrile, N,N-dimethylformamide or dimethylsulfoxyde, at a temperature ranging from about –10° C. to reflux.

From the foregoing, it is clear to the person skilled in the art that any of the above compounds of formula (I), (V) and (VIII) may be conveniently converted into other derivatives (I), (V) or (VIII) also by properly reacting functional groups other than the R, R₁ or X groups, extensively described above, according to conventional synthetic organic methods.

As an example, the above compounds (I) or (VIII) having R₂ equal to —CH₂OH or —OH, R other than hydrogen, and R₁ and X as above defined, can be reacted with a compound of formula (XVI)

R'—Y  (XVI)

wherein R', being as defined above is other than hydrogen and Y is a suitable leaving group as defined above, so as to obtain the corresponding compounds having R₂ as —CH₂OR' or OR' group.

This latter reaction can be carried out in the presence of a base such as sodium hydride, N,N-diisopropylethylamine or pyridine, in a suitable solvent, such as toluene, dichloromethane, chloroform, diethyl ether, tetrahydrofuran, acetonitrile, or N,N-dimethylformamide, at a temperature ranging from about –10° C. to reflux.

As it will be really appreciated by the person skilled in the art when preparing the compounds of formula (I) object of the invention, optional functional groups within both the staring materials or the intermediates thereof and which could give rise to unwanted side reactions, need to be properly protected according to conventional techniques. Likewise, the conversion of these latter into the free deprotected compounds may be carried out according to known procedures.

All of the compounds of formula (II), (III), (VI), (IX), (X), (XI), (XII), (XIII), (XIV), (XV) and (XVI) according to the process object of the invention, comprehensive of any variant thereof, are known or can be obtained according to known methods.

In particular, the compounds of formula (III), (VI), (IX), (X), (XI), (XII), (XIII), (XIV), (XV), (XVI), and (XVII) are commercially available or readily prepared according to conventional methods; the compounds of formula (II), instead, can be prepared by oxidising a compound of formula (XVII)

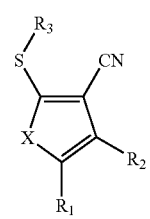

(XVII)

wherein R₁, R₂ and X are as above defined and R₃ is a lower alkyl group, according to conventional methods reported in the literature. As an example, the reaction can be carried in the presence of an opportune oxidizing agent such as, for instance, hydrogen peroxide, 3-chloroperoxybenzoic acid, oxone, in a suitable solvent such as, for instance, dichloromethane, DMF, acetone, toluene, acetonitrile, methanol, ethanol, water, acetic acid, at a temperature ranging from about –10° C. to reflux and for a time varying from about 30 minutes to about 4 days.

Compounds of formula (XVII) wherein R₁, R₃ and X are as above defined and R₂ is a hydrogen atom can be prepared by working in analogy to the procedure described by Wilson K. J. et al., in J. Bioorg. Med. Chem. Lett. 11 (2001), 915-918, starting from a compound of formula (XVIII)

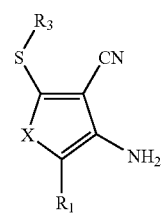

(XVIII)

The compounds of formula XVII wherein R₁, R₃ and X are as above defined and R₂ is other than a hydrogen atom can be prepared by treating a compound of formula (XVIII) with sodium nitrite, and by subsequently reacting the thus obtained-diazonium salt according to conventional methods in order to obtain the desired R₂ substituents.

Also the compounds of formula (XVIII) wherein $R_1$ is —COOMe, $R_3$ is a methyl group and X is S, can be prepared according to the aforementioned procedures described by Wilson K. J. et al., by starting from a compound of formula (XV).

The corresponding compounds of formula (XVIII) wherein $R_1$ is —COOR', —$SO_2$R', —$SO_2$NHR' or $SO_2$NR'R", and $R_3$ and X are as above defined, can be also prepared analogously by using the aforementioned procedures described by Wilson K. J. et al.

A compound of formula (XVIII) wherein $R_1$ is —COOtBu, can be conveniently prepared by the corresponding compound of formula (XVIII) wherein $R_1$ is —COOMe by using standard procedures well known in the art.

A compound of formula (XVIII) wherein $R_1$ is —COOR', —$SO_2$R', —$SO_2$NHR' or $SO_2$NR'R", and $R_3$ and X are as above defined, can be conveniently prepared by reacting a compound of formula (XIX)

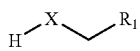

(XIX)

wherein $R_1$ and X are as defined above, with a compound of formula (XX)

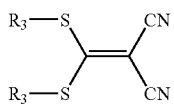

(XX)

wherein $R_3$ is as defined above.

This latter reaction can be carried out in the presence of a base, such as triethylamine, N,N-diisopropylethylamine, pyridine or sodium hydride in a suitable solvent such as toluene, diethyl ether, tetrahydrofuran, acetonitrile, dimethyl sulfoxide or N,N-dimethylformamide, at a temperature ranging from about 10° C. to reflux and for a time varying from about 30 minutes to about 96 hours.

In a further example, a compound of formula (XVIII) wherein $R_1$ is R', and $R_3$ and X are as above defined can be conveniently prepared by reaction of a compound of formula (XXI)

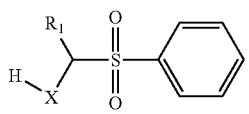

(XXI)

wherein $R_1$ is R' and X is as defined above, with a compound of formula (XX) as defined above. The reaction can be carried out in the presence of a base such as triethylamine, N,N-diisopropylethylamine, pyridine or sodium hydride in a suitable solvent such as toluene, diethyl ether, tetrahydrofuran, acetonitrile, dimethyl sulfoxide or N,N-dimethylformamide, at a temperature ranging from about 10° C. to reflux and for a time varying from about 30 minutes to about 96 hours and, subsequently, by treating the obtained product with zinc powder in acetic acid or magnesium powder in methanol, at a temperature ranging from about 10° C. to 60° C. and for a time varying from about 30 minutes to about 96 hours.

Finally, from all of the above, it is also clear to the person skilled in the art that the compounds of formula (I) of the invention can be also prepared by performing the reactions described above in a combinatorial fashion.

As an example, the compounds of formula (VII) supported onto resin particles, prepared as above described, may be reacted with a variety of compounds of formula from (IX) to (XVI) so as to obtain thousands of different compounds of formula (VIII), according to combinatorial chemistry methods. These latter derivatives, in their turn, may be then conveniently converted into the derivatives of formula (I) of the invention.

It is therefore a further object of the invention a combinatorial chemical library comprising a plurality of members of formula (VIII)

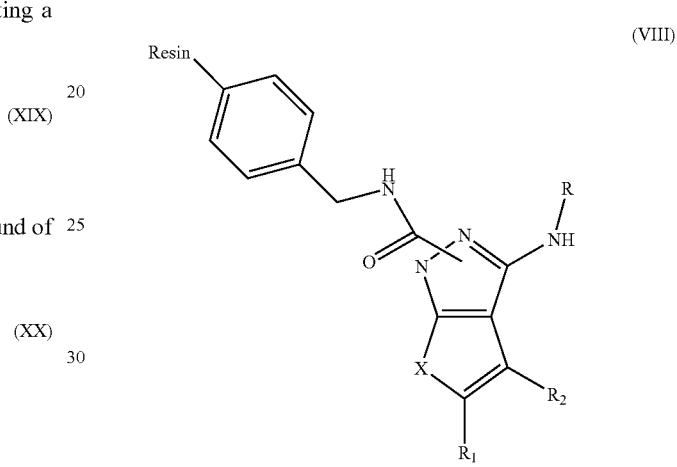

(VIII)

wherein
X is NR', O, S, SO or $SO_2$;
each of R and $R_1$, being the same or different, is independently a hydrogen atom or an optionally substituted group selected from R', —COR', —COOR', —CONHR', —CONR'R", —$SO_2$R', —$SO_2$NHR' or —$SO_2$NR'R"; wherein each of R' and R", being the same or different, is independently selected from hydrogen or an optionally further substituted straight or branched $C_1$-$C_6$ alkyl, heterocyclyl, aryl or aryl-$C_1$-$C_6$ alkyl group;
$R_2$ is an optionally substituted group selected from R', —$CH_2$OR' and OR', wherein R' is as above defined; and the pharmaceutically acceptable salts thereof.

Preferably, the above resin is a polystrenic resin, in particular a methylisocyanate polystyrene resin.

The said resin may be then cleaved by working according to conventional methods so as to give rise to a plurality of compounds of formula (I).

Therefore, it is a further object of the invention a chemical library of compounds comprising two or more derivatives of formula (I)

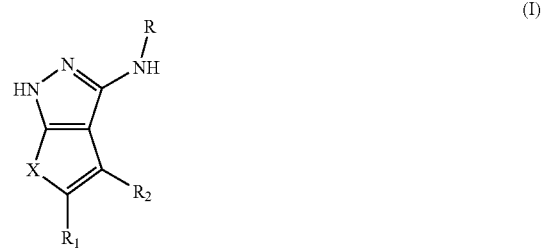

(I)

wherein

X is NR', O, S, SO or $SO_2$;

each of R and $R_1$, being the same or different, is independently a hydrogen atom or an optionally substituted group selected from R', —COR', —COOR', —CONHR', —CONR'R", —$SO_2$R', —$SO_2$NHR' or —$SO_2$NR'R"; wherein each of R' and R", being the same or different, is independently selected from hydrogen or an optionally further substituted straight or branched $C_1$-$C_6$ alkyl, heterocyclyl aryl or aryl-$C_1$-$C_6$ alkyl group;

$R_2$ is an optionally substituted group selected from R', —$CH_2$OR' and OR', wherein R' is as above defined; and the pharmaceutically acceptable salts thereof.

From all of the above, it is clear to the skilled person that once a library of compounds of formula (I) is thus prepared, for instance consisting of several hundreds of members, the said library can be very advantageously used for screening towards given kinases, as formerly reported.

See, for a general reference to libraries of compounds and uses thereof as tools for screening biological activities, J. Med. Chem. 1999, 42, 2373-2382; and Bioorg. Med. Chem. Lett. 10 (2000), 223-226.

Pharmacology

The compounds of formula (I) are active as protein kinase inhibitors and are therefore useful, for instance, to restrict the unregulated proliferation of tumor cells.

In particular they are active as cyclin dependent kinase (cdk) inhibitors and also as inhibitors of other protein kinases such as, for instance, protein kinase C in different isoforms, Met, PAK-4, PAK-5, ZC-1, STLK-2, DDR-2, Aurora 1, Aurora 2, Bub-1, PLK, Chk1, Chk2, HER2, raf1, MEK1, MAPK, EGF-R, PDGF-R, FGF-R, IGF-R, VEGF-R, PI3K, wee1 kinase, Src, Abl, Akt, ILK, MK-2, IKK-2, Cdc7, Nek, and thus to be effective in the treatment of diseases associated with other protein kinases.

In therapy, they may be used in the treatment of various tumors, such as those formerly reported, as well as in the treatment of other cell proliferative disorders such as psoriasis, vascular smooth cell proliferation associated with atherosclerosis and post-surgical stenosis and restenosis and in the treatment of Alzheimer's disease.

The inhibiting activity of putative cdk/cyclin inhibitors and the potency of selected compounds is determined through a method of assay based on the use of the SPA technology (Amersham Pharmacia Biotech).

The assay consists of the transfer of radioactivity labelled phosphate moiety by the kinase to a biotinylated substrate. The resulting 33P-labelled biotinylated product is allowed to bind to streptavidin-coated SPA beads (biotin capacity 130 pmol/mg), and light emitted was measured in a scintillation counter.

Inhibition Assay of cdk2/Cyclin A Activity

Kinase reaction: 4 µM in house biotinylated histone H1 (Sigma # H-5505) substrate, 10 µM ATP (0.1 microCi $P^{33}\gamma$-ATP), 1.1 nM Cyclin A/CDK2 complex, inhibitor in a final volume of 30 µl buffer (TRIS HCl 10 mM pH 7.5, $MgCl_2$ 10 mM, DTT 7.5 mM+0.2 mg/ml BSA) were added to each well of a 96 U bottom. After incubation for 60 min at room temperature, the reaction was stopped by addition of 100 µl PBS buffer containing 32 mM EDTA, 500 µM cold ATP, 0.1% Triton X100 and 10 mg/ml streptavidin coated SPA beads. After 20 min incubation, 110 µL of suspension were withdrawn and transferred into 96-well-OPTIPLATEs containing 100 µl of 5M CsCl. After 4 hours, the plates were read for 2 min in a Packard TOP-Count radioactivity reader.

IC50 determination: inhibitors were tested at different concentrations ranging from 0.0015 to 10 µM. Experimental data were analyzed by the computer program GraphPad Prizm using the four parameter logistic equation:

$$y=\text{bottom}+(\text{top}-\text{bottom})/(1+10^{((\log IC50-x)*\text{slope})})$$

where x is the logarithm of the inhibitor concentration, y is the response; y starts at bottom and goes to top with a sigmoid shape.

Ki Calculation:

Experimental method: Reaction was carried out in buffer (10 mM Tris, pH 7.5, 10 mM $MgCl_2$, 0.2 mg/ml BSA, 7.5 mM DTT) containing 3.7 nM enzyme, histone and ATP (constant ratio of cold/labeled ATP 1/3000). Reaction was stopped with EDTA and the substrate captured on phosphomembrane (Multiscreen 96 well plates from Millipore). After extensive washing, the multiscreen plates were read on a top counter. Control (time zero) for each ATP and histone concentrations was measured.

Experimental design: Reaction velocities are measured at four ATP, substrate (histone) and inhibitor concentrations. An 80-point concentration matrix was designed around the respective ATP and substrate Km values, and the inhibitor IC50 values (0.3, 1, 3, 9 fold the Km or IC50 values). A preliminary time course experiment in the absence of inhibitor and at the different ATP and substrate concentrations allows the selection of a single endpoint time (10 min) in the linear range of the reaction for the Ki determination experiment.

Kinetic parameter estimates: Kinetic parameters were estimated by simultaneous nonlinear least-square regression using [Eq. 1] (competitive inhibitor respect to ATP, random mechanism) using the complete data set (80 points):

$$v = \frac{Vm \cdot A \cdot B}{\alpha \cdot Ka \cdot Kb + \alpha \cdot Ka \cdot B + a \cdot Kb \cdot A + A \cdot B + \alpha \cdot \frac{Ka}{Ki} \cdot I \cdot \left(Kb + \frac{B}{\beta}\right)} \quad [\text{Eq. 1}]$$

where A=[ATP], B=[Substrate], I=[inhibitor], Vm=maximum velocity, Ka, Kb, Ki the dissociation constants of ATP, substrate and inhibitor respectively. α and β the cooperativity factor between substrate and ATP binding and substrate and inhibitor binding respectively.

In addition the selected compounds are characterized on a panel of ser/thre kinases strictly related to cell cycle (cdk2/cyclin E, cdk1/cyclin B1, cdk5/p25, cdk4/cyclin D1), and also for specificity on MAPK, PKA, EGFR, IGF1-R, Aurora-2 and Cdc 7.

Inhibition Assay of cdk2/Cyklin E Activity

Kinase reaction: 10 µM in house biotinylated histone H1 (Sigma # H-5505) substrate, 30 µM ATP (0.3 microCi $P^{33}\gamma$-ATP), 4 ng GST-Cyclin E/CDK2 complex, inhibitor in a final volume of 30 µl buffer (TRIS HCl 10 mM pH 7.5, $MgCl_2$ 10 mM, DTT 7.5 mM+0.2 mg/ml BSA) were added to each well of a 96 U bottom. After incubation for 60 min at room temperature, the reaction was stopped by addition of 100 µl PBS buffer containing 32 mM EDTA, 500 µM cold ATP, 0.1% Triton X100 and 10 mg/ml streptavidin coated SPA beads. After 20 min incubation, 110 µL of suspension were withdrawn and transferred into 96-well OPTIPLATEs containing 100 µl of 5M CsCl. After 4 hours, the plates were read for 2 min in a Packard TOP-Count radioactivity reader.

IC50 determination: see above

Inhibition Assay of cdk1/Cyclin B1 Activity

Kinase reaction: 4 µM in house biotinylated histone H1 (Sigma # H-5505) substrate, 20 µM ATP (0.2 microCi $P^{33}\gamma$-ATP), 3 ng Cyclin B/CDK1 complex, inhibitor in a final volume of 30 µl buffer (TRIS HCl 10 mM pH 7.5, MgCl$_2$ 10 mM, DTT 7.5 mM+0.2 mg/ml BSA) were added to each well of a 96 U bottom. After 20 min at r.t. incubation, reaction was stopped by 100 µl PBS+32 mM EDTA+0.1% Triton X-100+ 500 µM ATP, containing 1 mg SPA beads. Then a volume of 110 µl is transferred to Optiplate. After 20 min. incubation for substrate capture, 100 µl 5M CsCl were added to allow statification of beads to the top of the Optiplate and let stand 4 hours before radioactivity counting in the Top-Count instrument.

IC50 determination: see above

Inhibition Assay of cdk5/p25 Activity

The inhibition assay of cdk5/p25 activity is performed according to the following protocol.

Kinase reaction: 10 µM biotinylated histone H1 (Sigma # H-5505) substrate, 30 µM ATP (0.3 microCi $P^{33}\gamma$-ATP), 15 ng CDK5/p25 complex, inhibitor in a final volume of 30 µl buffer (TRIS HCl 10 mM pH 7.5, MgCl$_2$ 10 mM, DTT 7.5 mM+0.2 mg/ml BSA) were added to each well of a 96 U bottom. After incubation for 35 min at room temperature, the reaction was stopped by addition of 100 µl PBS buffer containing 32 mM EDTA, 500 µM cold ATP, 0.1% Triton X100 and 10 mg/ml streptavidin coated SPA beads. After 20 min incubation, 110 µL of suspension were withdrawn and transferred into 96-well OPTIPLATEs containing 100 µl of 5M CsCl. After 4 hours, the plates were read for 2 min in a Packard TOP-Count radioactivity reader.

IC50 determination: see above

Inhibition Assay of cdk4/Cyclin D1 Activity

Kinase reaction: 0.4 uM µM mouse GST-Rb (769-921) (# sc-4112 from Santa Cruz) substrate, 10 µM ATP (0.5 µCi $P^{33}\gamma$-ATP), 100 ng of baculovirus expressed GST-cdk4/GST-Cyclin D1, suitable concentrations of inhibitor in a final volume of 50 µl buffer (TRIS HCl 10 mM pH 7.5, MgCl$_2$ 10 mM, 7.5 mM DTT+ 0.2 mg/ml BSA) were added to each well of a 96 U bottom well plate. After 40 min at 37° C. incubation, reaction was stopped by 20 µl EDTA 120 mM.

Capture: 60 µl were transferred from each well to Multi-Screen plate, to allow substrate binding to phosphocellulose filter. Plates were then washed 3 times with 150 µl/well PBS Ca$^{++}$/Mg$^{++}$ free and filtered by MultiScreen filtration system.

Detection: filters were allowed to dry at 37° C., then 100 µl/well scintillant were added and $^{33}P$ labeled Rb fragment was detected by radioactivity counting in the Top-Count instrument.

IC50 determination: see above

Inhibition Assay of MAPK Activity

Kinase reaction: 10 µM in house biotinylated MBP (Sigma # M-1891) substrate, 15 µM ATP (0.15 microCi $P^{33}\gamma$-ATP), 30 ng GST-MAPK Upstate Biothecnology # 14-173), inhibitor in a final volume of 30 µl buffer (TRIS HCl 10 mM pH 7.5, MgCl$_2$ 10 mM, DTT 7.5 mM+0.2 mg/ml BSA) were added to each well of a 96 U bottom. After incubation for 35 min at room temperature, the reaction was stopped by addition of 100 µl PBS buffer containing 32 mM EDTA, 500 µM cold ATP, 0.1% Triton X100 and 10 mg/ml streptavidin coated SPA beads. After 20 min incubation, 110 µL of suspension were withdrawn and transferred into 96-well OPTIPLATEs containing 100 µl of 5M CsCl. After 4 hours, the plates were read for 2 min in a Packard TOP-Count radioactivity reader.

IC50 determination: see above

Inhibition Assay of PKA Activity

Kinase reaction: 10 µM in house biotinylated histone H1 (Sigma # H-5505) substrate, 10 µM ATP (0.2 microM $P^{33}\gamma$-ATP), 0.45 U PKA (Sigma # 2645), inhibitor in a final volume of 30 µl buffer (TRIS HCl 10 mM pH 7.5, MgCl$_2$ 10 mM, DTT 7.5 mM+0.2 mg/ml BSA) were added to each well of a 96 U bottom. After incubation for 90 min at room temperature, the reaction was stopped by addition of 100 µl PBS buffer containing 32 mM EDTA, 500 µM cold ATP, 0.1% Triton X100 and 10 mg/ml streptavidin coated SPA beads. After 20 min incubation, 110 µL of suspension were withdrawn and transferred into 96-well OPTIPLATEs containing 100 µl of 5M CsCl. After 4 hours, the plates were read for 2 min in a Packard TOP-Count radioactivity reader.

IC50 determination: see above

Inhibition Assay of EGFR Activity

Kinase reaction: 10 µM in house biotinylated MBP (Sigma # M-1891) substrate, 2 µM ATP (0.04 microCi $P^{33}\gamma$-ATP), 36 ng insect cell expressed GST-EGFR, inhibitor in a final volume of 30 µl buffer (Hepes 50 mM pH 7.5, MgCl$_2$ 3 mM, MnCl$_2$ 3 mM, DTT 1 mM, NaVO$_3$ 3 µM, +0.2 mg/ml BSA) were added to each well of a 96 U bottom. After incubation for 20 min at room temperature, the reaction was stopped by addition of 100 µl PBS buffer containing 32 mM EDTA, 500 µM cold ATP, 0.1% Triton X100 and 10 mg/ml streptavidin coated SPA beads. After 20 min incubation, 110 µL of suspension were withdrawn and transferred into 96-well OPTIPLATEs containing 100 µl of 5M CsCl. After 4 hours, the plates were read for 2 min in a Packard TOP-Count radioactivity reader.

IC50 determination: see above

Inhibition Assay of XGF1-R Activity

The inhibition assay of IGF1-R activity is performed according to the following protocol.

Enzyme activation: IGF1-R must be activated by autophosphorylation before starting the experiment. Just prior to the assay, a concentrated enzyme solution (694 nM) is incubated for half a hour at 28° C. in the presence of 100 µM ATP and then brought to the working dilution in the indicated buffer.

Kinase reaction: 10 µM biotinylated IRS1 peptide (PRIMM) substrate, 0-20 µM inhibitor, 6 µM ATP, 1 microCi $^{33}P$-ATP, and 6 nM GST-IGF1-R (pre-incubated for 30 min at room temperature with cold 60 µM cold ATP) in a final volume of 30 µl buffer (50 mM HEPES pH 7.9, 3 mM MnCl$_2$, 1 mM DTT, 3 µM NaVO$_3$) were added to each well of a 96 U bottom well plate. After incubation for 35 min at room temperature, the reaction was stopped by addition of 100 µl PBS buffer containing 32 mM EDTA, 500 µM cold ATP, 0.1% Triton X100 and 10 mg/ml streptavidin coated SPA beads. After 20 min incubation, 110 µL of suspension were withdrawn and transferred into 96-well OPTIPLATEs containing 100 µl of 5M CsCl. After 4 hours, the plates were read for 2 min in a Packard TOP-Count radioactivity reader.

Inhibition Assay of Aurora-2 Activity

Kinase reaction: 8 µM biotinylated peptide (4 repeats of LRRWSLG), 10 µM ATP (0.5 uCi $P^{33}\gamma$-ATP), 7.5 ng Aurora 2, inhibitor in a final volume of 30 µl buffer (HEPES 50 mM pH 7.0, MgCl$_2$ 10 mM, 1 mM DTT, 0.2 mg/ml BSA, 3 µM orthovanadate) were added to each well of a 96 U bottom well plate. After 60 minutes at room temperature incubation, reaction was stopped and biotinylated peptide captured by adding 100 µl of bead suspension.

Stratification: 100 μl of CsCl2 5 M were added to each well and let stand 4 hour before radioactivity was counted in the Top-Count instrument.

IC50 determination: see above

Inhibition Assay of Cdc7/dbf4 Activity

The inhibition assay of Cdc7/dbf4 activity is performed according to the following protocol.

The Biotin-MCM2 substrate is trans-phosphorylated by the Cdc7/Dbf4 complex in the presence of ATP traced with $\gamma^{33}$-ATP. The phosphorylated Biotin-MCM2 substrate is then captured by Streptavidin-coated SPA beads and the extent of phosphorylation evaluated by β counting.

The inhibition assay of Cdc7/dbf4 activity was performed in 96 wells plate according to the following protocol.

To each well of the plate were added:
- 10 μl substrate (biotinylated MCM2, 6 μM final concentration)
- 10 μl enzyme (Cdc7/Dbf4, 17.9 nM final concentration)
- 10 μl test compound (12 increasing concentrations in the nM to μM range to generate a dose-response curve)
- 10 μl of a mixture of cold ATP (2 μM final concentration) and radioactive ATP (1/5000 molar ratio with cold ATP) was then used to start the reaction which was allowed to take place at 37° C.

Substrate, enzyme and ATP were diluted in 50 mM HEPES pH 7.9 containing 15 mM $MgCl_2$, 2 mM DTT, 3 μM $NaVO_3$, 2 mM glycerophosphate and 0.2 mg/ml BSA. The solvent for test compounds also contained 10% DMSO.

After incubation for 60 minutes, the reaction was stopped by adding to each well 100 μl of PBS pH 7.4 containing 50 mM EDTA, 1 mM cold ATP, 0.1% Triton X100 and 10 mg/ml streptavidin coated SPA beads.

After 20 min incubation, 110 μL of suspension were withdrawn and transferred into 96-well OPTIPLATEs containing 100 μl of 5M CsCl. After 4 hours, the plates were read for 2 min in a Packard TOP-Count radioactivity reader.

IC50 determination: see above.

In view of the above biological activities the compounds of the invention can be useful in therapy, for instance, to restrict the unregulated proliferation of tumor cells. More specifically, the bicyclo-pyranzoles of the invention can be useful in the treatment of a variety of cancers including, but not limited to carcinoma of several organs, tissues and glands such as bladder, breast, colon, kidney, liver, lung, including small cell lung cancers esophagus, gall-bladder, ovary, pancreas, stomach, cervix, thyroid, prostate, and skin, including squamous cell carcinoma; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthomas, thyroid follicular cancer and Kaposi's sarcoma. Due to the key role of PKs in the regulation of cellular proliferation, the bicyclo-pyrazoles of the invention can also be useful in the treatment of a variety of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis. The compounds of the invention can be useful in the treatment of Alzheimer's disease, as suggested by the fact that cdk5 is involved in the phosphorylation of tau protein (J. Biochem., 117, 741-749, 1995). The compounds of the invention, as modulators of apoptosis, may also be useful in the treatment of cancer, viral infections, prevention of AIDS development in HIV-infected individuals, autoimmune diseases and neurodegenerative disorders. The compounds of the invention may be useful in inhibiting tumor angiogenesis and metastasis.

The compounds of the invention are suitable for administration to a mammal, e.g. to humans, by the usual routes. The dosage level depends as usual upon the age, weight, conditions of the patient and the administration route.

For example, a suitable dosage adopted for oral administration of the compounds of the invention, for instance, N-benzyl-3-{[(4-ethylpiperazin-1-yl)benzoyl]amino}-1H-thieno[3,2-c]pyrazole-5-carboxamide, may range from about 5 to about 500 mg pro dose, from 1 to 5 times daily.

The compounds of the invention can be administered in a variety of dosage forms, e.g. orally, in the form of tablets, capsules, sugar or film coated tablets, liquid solutions or suspensions; rectally in the form of suppositories; parenterally, e.g. intramuscularly, by intravenous and/or intrathecal and/or intraspinal injection or infusion; or by transdermal administration.

In addition, the compounds of the invention can be administered either as single agents or, alternatively, in a combination therapy method comprising additional anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors, in particular celecoxib, rofecoxib, parecoxib and valdecoxib), metallomatrixprotease inhibitors, telomerase inhibitors, tyrosine kinase inhibitors, anti-growth factor receptor agents, anti-HER agents, anti-EGFR agents, anti-angiogenesis agents, farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of his invention within the dosage range described above and the other pharmaceutically active agent within the approved dosage range.

Compounds of formula (I) may be used sequentially with known anticancer agents when a combination formulation is inappropriate.

The invention, therefore, also provides a method for treating a mammal, including humans, suffering from a disease caused by and/or associated with an altered (disregulated) protein kinase activity, comprising administering to said mammal in need thereof a therapeutically effective amount of a bicyclo-pyrazole compound of formula (I), or a pharmaceutically acceptable salt thereof, while undergoing simultaneous, separate or sequential anticancer treatments.

A further object of the invention is the use of a compound of formula (I), or a pharmaceutically acceptable salt thereof, in the manufacture of a medicament for treating a disease caused by and/or associated with an altered protein kinase activity, in a patient undergoing a simultaneous, separate or sequential anticancer treatments.

The present invention also includes pharmaceutical compositions comprising a compound of formula (I) or a pharmaceutically acceptable salt thereof in association with a pharmaceutically acceptable excipient, which can be a carrier or a diluent.

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, sucrose, cellulose, corn starch or potato starch; lubricants, e.g. silica, talc, stearic, magnesium or calcium stearate, and/or polyethylene glycols; binding agents, e.g. starches, arabic gum, gelatine, methylcellulose, carboxymethylcellulose or polyvinyl pyrrolidone; disaggregating agents, e.g. a starch, alginic, alginates or sodium starch glycolate; effervescing mixtures; dyestuffs; sweeteners; wetting agents such as lecithin, polysorbates, laurylsulphates; and, in, general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions may contain as carrier, for example, sterile water or preferably they may be in the form of sterile, aqueous, isotonic saline solutions or they may contain as a carrier propylene glycol.

The suppositories may contain together with the active compound a pharmaceutically acceptable carrier, e.g. cocoa butter, polyethylene glycol, a polyoxyethylene sorbitan fatty ester surfactant or lecithin.

The following examples are herewith intended to illustrate, without posing any limitation to, the present invention.

SYNTHETIC EXAMPLES

The following HPLC methods were used in the analysis of the compounds as specified in the synthetic examples set forth below. As used herein, the term "Rt" refers to the retention time for the compound using the HPLC method specified.

Method A

HPLC/MS was performed on a Waters X Terra RP 18 (4.6×50 mm, 3.5 μm) column using a Waters 2790 HPLC system equipped with a 996 Waters PDA detector and a Micromass mod. ZQ single quadrupole mass spectrometer, equipped with an electrospray (ESI) ion source. Mobile phase A was ammonium acetate 5 mM buffer (pH 5.5 with acetic acid/acetonitrile 95:5), and Mobile phase B was H2O/acetonitrile (5:95). Gradient from 10 to 90% B in 8 minutes, hold 90% B 2 min. UV detection at 220 nm and 254 nm. Flow rate 1 ml/min. Injection volume 10 μl. Full scan, mass range from 100 to 800 amu. Capillary voltage was 2.5 KV; Source temp was 120° C.; Cone was 10 V. Retention Times (HPLC r.t.) are given in minutes at 220 nm or 254 nm. Mass are given as m/z ratio.

Method B

HPLC/MS was performed on a Hypersil C18 BDS (2×50 mm, 5 μm) column using a Hewlett Packard 1312A HPLC system equipped with a Polymer Labs PL1000 Evaporative Light Scattering detector and a Micromass ZMD mass spectrometer, equipped with an electrospray (ESI) ion source. Mobile phase A was aqueous solution of trifluoroacetic acid (0.1% v/v), and Mobile phase B was acetonitrile solution of trifluoroacetic acid (0.1% v/v). Gradient from 0 to 95% B in 1.8 minutes, hold 95% B for 0.3 min. Flow rate 1 ml/min. Injection volume 3 μl. Full scan, mass range from 150 to 800 amu. Source temp was 140° C.; Cone was 25 V. Retention Times (HPLC r.t.) are given in minutes. Mass are given as m/z ratio.

Example 1

4-cyano-5-(methylthio)thiophene-2-carboxylic acid

Aqueous sodium hydroxide (20% w/w solution, 9 mL) was added to a solution of ethyl 4-cyano-5-(methylthio)thiophene-2-carboxylate (10 g, 44 mmol) in 1,4-dioxane (100 mL) at 5° C.

After stirring for 4 hours at room temperature, water (500 mL) was added to the reaction mixture and the pH was adjusted to pH about 2.5 by adding 2N aqueous hydrochloric acid. A white solid was separated by filtration, washed with water, and dried under vacuum to give 8.5 g of the title compound.

Chromatographic method A, Rf 2.4; [M+H]$^+$ 200.

Example 2 tert-butyl 4-cyano-5-(methylthio)thiophene-2-carboxylate

A mixture of 4-cyano-5-(methylthio)thiophene-2-carboxylic acid (2.0 g, 10 mmol), benzyltrimethylammonium chloride (2.25 g, 10 mmol), tertbutyl bromide (54 mL, 480 mmol), and anhydrous potassium carbonate (36 g, 260 mmol) in dimethylacetamide (100 mL) was stirred at 60° C. for 6 hours.

After cooling the mixture was diluted with ethyl acetate (400 mL) and washed with water. Organic layer was dried and evaporated under reduced pressure to give a residue which was purified by chromatography (eluent ethyl acetate/n-hexane 3:1) yielding 1.5 g of the title compound.

Chromatographic method A, Rf 7.4; [M+H]$^+$ 256.

Example 3 tert-butyl 4-cyano-5-(methylsulfonyl)thiophene-2-carboxylate

A mixture of tert-butyl 4-cyano-5-(methylthio)thiophene-2-carboxylate (1.4 g, 5.5 mmol) and oxone (14.4 g, 21.5 mmol) in dimethylformamide (100 mL) was stirred at room temperature for 16 hours. The reaction mixture was then poured into ice/water (400 mL) and extracted with ethyl acetate. Organic layer was washed with water, dried over anhydrous sodium sulfate and evaporated to give 1.5 g of the title compound.

Chromatographic method A, Rf 6.2; [M+H]$^+$ 288.

Example 4 tert-butyl 4-cyano-5-hydrazinothiophene-2-carboxylate

A mixture of tert-butyl 4-cyano-5-methylsulfonyl) thiophene-2-carboxylate (2.0 g, 7.0 mmol) and hydrazine hydrate (1.7 mL) in methyl alcohol (30 mL) was stirred at 60° C. for 2 hours. The reaction mixture was diluted with ethyl acetate (100 mL) and washed with water. Organic layer was separated, dried over anhydrous sodium sulfate, and evaporated. Purification by chromatography (n-hexane/ethyl acetate 3:2) gave 1 g of the title compound.

Chromatographic method A, Rf 5.6; [M+H]$^+$ 240.

Example 5 tert-butyl 3-amino-1H-thieno[2,3-c]pyrazole-5-carboxylate

A mixture of tert-butyl 4-cyano-5-hydrazinothiophene-2-carboxylate (1.0 g, 4.2 mmol) and hydrochloric acid (0.7 mL of 37% solution) in methyl alcohol (15 mL) was stirred at room temperature for 14 hours. The reaction mixture was diluted with ethyl acetate (50 mL) and washed with an aqueous solution of sodium bicarbonate. Organic layer was separated, dried over anhydrous sodium sulfate, and evaporated to give 0.9 g of the title compound.

Chromatographic method A, Rf 4.5; [M+H]$^+$ 240.

Example 6

By working as described in the previous examples and by starting from any suitable starting material, according to processes object of the invention, the following compounds of formula (I) can be obtained:

1. N-benzyl-3-[(4-fluorobenzoyl)amino]-1H-thieno[2,3-c]pyrazole-5-carboxamide;
2. N-ethyl-3-{[4-(4-ethylpiperazin-1-yl)benzoyl]amino}-1H-thieno[2,3-c]pyrazole-5-carboxamide;
3. 3-{[4-(4-ethylpiperazin-1-yl)benzoyl]amino}-N-isopropyl-1H-thieno[2,3-c]pyrazole-5-carboxamide;
4. N-benzyl-3-{[4-(4-ethylpiperazin-1-yl)benzoyl]amino}-1H-thieno[2,3-c]pyrazole-5-carboxamide;
5. N-{5-[(4-methylpiperazin-1-yl)carbonyl]-1H-thieno[2,3-c]pyrazol-3-yl}benzamide;
6. N-[5-morpholin ylcarbonyl)-1H-thieno[2,3-c]pyrazol-3-yl]benzamide;
7. 3-(benzoylamino)-N-2-morpholin-4-ylethyl)-1H-thieno[2,3-c]pyrazole-5-carboxamide;
8. 3-(benzoylamino)-N-phenyl-1H-thieno[2,3-c]pyrazole-5-carboxamide;
9. 3-(benzoylamino)-N-(2-methylphenyl)-1H-thieno[2,3-c]pyrazole-5-carboxamide;
10. 3-(benzoylamino)-N-(4-cyanophenyl)-1H-thieno[2,3-c]pyrazole-5-carboxamide;
11. 3-(benzoylamino)-N-(4-fluorophenyl)-1H-thieno[2,3-c]pyrazole-5-carboxamide;
12. 3-(benzoylamino)-N-(4-chlorophenyl)-1H-thieno[2,3-c]pyrazole-5-carboxamide;
13. 3-(benzoylamino)-N-(4-methoxyphenyl)1H-thieno[2,3-c]pyrazole-5-carboxamide;
14. 3-(benzoylamino)-N-(4-methylphenyl)-1H-thieno[2,3-c]pyrazole-5-carboxamide;
15. 3-(benzoylamino)-N-tert-butyl)-1H-thieno[2,3-c]pyrazole-5-carboxamide;
16. 3-(benzoylamino)-N-isopropyl-1H-thieno[2,3-c]pyrazole-5-carboxamide;
17. 3-benzoylamino)-N-ethyl-1H-thieno[2,3-c]pyrazole-5-carboxamide;
18. 2-fluoro-N-{5-[(4-methylpiperazin-1-yl)carbonyl]-1H-thieno[2,3-c]pyrazol-3-yl}benzamide;
19. 2-fluoro-N-[5-(morpholin-4-ylcarbonyl)-1H-thieno[2,3-c]pyrazol-3-yl]benzamide;
20. 3-[(2-fluorobenzoyl)amino]-N-(2-morpholin-4-ylethyl)-1H-thieno[2,3-c]pyrazole-5-carboxamide;
21. 3-[(2-fluorobenzoyl)amino]-N-phenyl-1H-thieno[2,3-c]pyrazole-5-carboxamide;
22. 3-[(2-fluorobenzoyl)amino]-N-(2-methylphenyl)-1H-thieno[2,3-c]pyrazole-5-carboxamide;
23. N-(4-cyanophenyl)-3-[(2-fluorobenzoyl)amino]-1H-thieno[2,3-c]pyrazole-5-carboxamide;
24. 3-[(2-fluorobenzoyl)amino]-N-(4-fluorophenyl)-1H-thieno[2,3-c]pyrazole-5-carboxamide;
25. N-(4-chlorophenyl)-3-[(2-fluorobenzoyl)amino]-1H-thieno[2,3-c]pyrazole-5-carboxamide;
26. 3-[(2-fluorobenzoyl)amino]-N-(4-methoxyphenyl)-1H-thieno[2,3-c]pyrazole-5-carboxamide;
27. 3-[(2-fluorobenzoyl)amino]-N-(4-methylphenyl)-1H-thieno[2,3-c]pyrazole-5-carboxamide;
28. N-tert-butyl)-3-[(2-fluorobenzoyl)amino]-1H-thieno[2,3-c]pyrazole-5-carboxamide;
29. 3-[(2-fluorobenzoyl)amino]-N-isopropyl-1H-thieno[2,3-c]pyrazole-5-carboxamide;
30. N ethyl-3-[(2-fluorobenzoyl)amino]-1H-thieno[2,3-c]pyrazole-5-carboxamide;
31. 2-chloro-N-{5-[(4-methylpiperazin-1-yl)carbonyl]-1H-thieno[2,3-c]pyrazol-3-yl}benzamide;
32. 2-chloro-N-[5-(morpholin-4-ylcarbonyl)-1H-thieno[2,3-c]pyrazol-3-yl]benzamide;
33. 3-[(2-chlorobenzoyl)amino]-N-(2-morpholinylethyl)-1H-thieno[2,3-c]pyrazole-5-carboxamide;
34. 3-[(2-chlorobenzoyl)amino]-N-phenyl-1H-thieno[2,3-c]pyrazole-5-carboxamide;
35. 3-[(2-chlorobenzoyl)amino]-N-(2-methylphenyl)-1H-thieno[2,3-c]pyrazole-5-carboxamide;
36. 3-[(2-chlorobenzoyl)amino]-N-(4-cyanophenyl)-1H-thieno[2,3-c]pyrazole-5-carboxamide;
37. 3-[(2-chlorobenzoyl)amino]-N-(4-fluorophenyl)-1H-thieno[2,3-c]pyrazole-5-carboxamide;
38. 3-[(2-chlorobenzoyl)amino]-N-(4-chlorophenyl)-1H-thieno[2,3-c]pyrazole-5-carboxamide;
39. 3-[(2-chlorobenzoyl)amino]-N-(4-methoxyphenyl)-1H-thieno[2,3-c]pyrazole-5-carboxamide;
40. 3-[(2-chlorobenzoyl)amino]-N-(4-methylphenyl)-1H-thieno[2,3-c]pyrazole-5-carboxamide;
41. N-(tert-butyl)-3-[(2-chlorobenzoyl)amino]-1H-thieno[2,3-c]pyrazole-5-carboxamide;
42. 3-[(2-chlorobenzoyl)amino]-N-isopropyl-1H-thieno[2,3-c]pyrazole-5-carboxamide;
43. 3-[(2-chlorobenzoyl)amino]-N-ethyl-1H-thieno[2,3-c]pyrazole-5-carboxamide;
44. 2-methoxy-N-{5-[(4-methylpiperazin-1-yl)carbonyl]-1H-thieno[2,3-c]pyrazol-3-yl}benzamide;
45. 2-methoxy-N-[5-(morpholin-4-ylcarbonyl)-1H-thieno[2,3]pyrazol-3-yl]benzamide;
46. 3-[(2-methoxybenzoyl)amino]-N-(2-morpholin-4-ylethyl)-1H-thieno[2,3-c]pyrazole-5-carboxamide;
47. 3-[(2-methoxybenzoyl)amino]-N-phenyl-1H-thieno[2,3-c]pyrazole-5-carboxamide;
48. 3-[(2-methoxybenzoyl)amino]-N-(2-methylphenyl)-1H-thieno[2,3-c]pyrazole-5-carboxamide;

49. N-(4-cyanophenyl)-3-[(2-methoxybenzoyl)amino]-1H-thieno[2,3-c]pyrazole-5-carboxamide;
50. N-(4-fluorophenyl)-3-[(2-methoxybenzoyl)amino]-1H-thieno[2,3-c]pyrazole-5-carboxamide;
51. N-(4-chlorophenyl)-3-[(2-methoxybenzoyl)amino]-1H-thieno[2,3c]pyrazole-5-carboxamide;
52. 3-[(2-methoxybenzoyl)amino]-N-(4-methoxyphenyl)-1H-thieno[2,3-c]pyrazole-5-carboxamide;
53. 3-[(2-methoxybenzoyl)amino]-N-(4-methylphenyl)-1H-thieno[2,3-c]pyrazole-5-carboxamide;
54. N-(tert-butyl)-3-[(2-methoxybenzoyl)amino]-1H-thieno[2,3-c]pyrazole-5-carboxamide;
55. N-isopropyl-3-[(2-methoxybenzoyl)amino]-1H-thieno[2,]pyrazole-5-carboxamide;
56. N-ethyl-3-[(2-methoxybenzoyl)amino]-1H-thieno[2,3-c]pyrazole-5-carboxamide;
57. 2-methyl-N-{5-[(4-methylpiperazin-1-yl)carbonyl]-1H-thieno[2,3-c]pyrazol-3-yl}benzamide;
58. 2-methyl-N-[5-(morpholin-4-ylcarbonyl)-1H-thieno[2,3-c]pyrazol-3-yl]benzamide;
59. 3-[(2-methylbenzoyl)amino]-N-(2-morpholin-4-yl-ethyl)-1H-thieno[2,3-c]pyrazole-5-carboxamide;
60. 3-[(2-methylbenzoyl)amino]-N-phenyl-1H-thieno[2,3-c]pyrazole-5 carboxamide;
61. 3-[(2-methylbenzoyl)amino]-N-(2-methylphenyl)-1H-thieno[2,3-c]pyrazole-5-carboxamide;
62. N-(4-cyanophenyl)-3-[(2-methylbenzoyl)amino]-1H-thieno[2,3-c]pyrazole-5-carboxamide;
63. N-(4-fluorophenyl)-3-[(2-methylbenzoyl)amino]-1H-thieno[2,3-c]pyrazole-5-carboxamide;
64. N-(4-chlorophenyl)-3-[(2-methylbenzoyl)amino]-1H-thieno[2,3-c]pyrazole-5-carboxamide;
65. N-(4-methoxyphenyl)-3-[(2-methylbenzoyl)amino]-1H-thieno[2,3-c]pyrazole-5-carboxamide;
66. 3-[(2-methylbenzoyl)amino]-N-(4-methylphenyl)-1H-thieno[2,3-c]pyrazole-5-carboxamide;
67. N-(tert-butyl)-3-[(2-methylbenzoyl)amino]-1H-thieno[2,3-c]pyrazole-5-carboxamide;
68. N-isopropyl-3-[(2-methylbenzoyl)amino]-1H-thieno[2,3-c]pyrazole-5-carboxamide;
69. N-ethyl-3-[(2-methylbenzoyl)amino]-1H-thieno[2,3-c]pyrazole-5-carboxamide;
70. 3-methyl-N-{5-[(4-methylpiperazin-1-yl)carbonyl]-1H-thieno[2,3-c]pyrazol-3-yl}benzamide;
71. 3-methyl-N-[5-(morpholin-4-ylcarbonyl)-1H-thieno[2,3-c]pyrazol-3-yl]benzamide;
72. 3-[(3-methylbenzoyl)amino]-N-(2-morpholin-4-yl-ethyl)-1H-thieno[2,3-c]pyrazole-5-carboxamide;
73. 3-[(3-methylbenzoyl)amino]-N-phenyl-1H-thieno[2,3-c]pyrazole-5-carboxamide;
74. 3-[3-methylbenzoyl)amino]-N-(2-methylphenyl)-1H-thieno[2,3-c]pyrazole-5-carboxamide;
75. N-(4-cyanophenyl)-3-[(3-methylbenzoyl)amino]-1H-thieno[2,3-c]pyrazole-5-carboxamide;
76. N-(4-fluorophenyl)-3-[(3-methylbenzoyl)amino]-1H-thieno[2,3-c]pyrazole-5-carboxamide;
77. N-(4-chlorophenyl)-3-[(3-methylbenzoyl)amino]-1H-thieno[2,3-c]pyrazole-5-carboxamide;
78. N-(4-methoxyphenyl)-3-[(3-methylbenzoyl)amino]-1H-thieno[2,3-c]pyrazole-5-carboxamide;
79. 3-[(3-methylbenzoyl)amino]-N-(4-methylphenyl)-1H-thieno[2,3-c]pyrazole-5-carboxamide;
80. N-(tert-butyl)-3-[(3-methylbenzoyl)amino]-1H-thieno[2,3-c]pyrazole-5-carboxamide;
81. N-isopropyl-3-[(3-methylbenzoyl)amino]-1H-thieno[2,3-c]pyrazole-5-carboxamide;
82. N-ethyl-3-[(3-methylbenzoyl)amino]-1H-thieno[2,3-c]pyrazole-5-carboxamide;
83. 4-fluoro-N-{5-[(4-methylpiperazin-1-yl)carbonyl]-1H-thieno[2,3-c]pyrazol-3-yl}benzamide;
84. 4-fluoro-N-[5-morpholin-4-ylcarbonyl)-1H-thieno[2,3-c]pyrazol-3-yl]benzamide;
85. 3-[(4-fluorobenzoyl)amino]-N-(2-morpholin-4-yl-ethyl)-1H-thieno[2,3-c]pyrazole-5-carboxamide;
86. 3-[(4-fluorobenzoyl)amino]-N-phenyl-1H-thieno[2,3-c]pyrazole-5-carboxamide;
87. 3-[(4-fluorobenzoyl)amino]-N-(2-methylphenyl)-1H-thieno[2,3-c]pyrazole-5-carboxamide;
88. N-(4-cyanophenyl)-3-[(4-fluorobenzoyl)amino]-1H-thieno[2,3-c]pyrazole-5-carboxamide;
89. 3-[(4-fluorobenzoyl)amino]-N-fluorophenyl)-1H-thieno[2,3-c]pyrazole-5-carboxamide;
90. N-(4-chlorophenyl)-3-[(4-fluorobenzoyl)amino]-1H-thieno[2,3-c]pyrazole-5-carboxamide;
91. 3-[(4-fluorobenzoyl)amino]-N-(4-methoxyphenyl)-1H-thieno[2,3-c]pyrazole-5-carboxamide;
92. 3-[(4-fluorobenzoyl)amino]-N-(4-methylphenyl)-1H-thieno[2,3-c]pyrazole-5-carboxamide;
93. N-(tert-butyl)-3-[(4-fluorobenzoyl)amino]-1H-thieno[2,3-c]pyrazolo-5-carboxamide;
94. 3-[(4-fluorobenzoyl)amino]-N-isopropyl-1H-thieno[2,3-c]pyrazole-5-carboxamide;
95. N-ethyl-3[(4-flurobenzoyl)amino]-1N-thieno[2,3-c]pyrazole-5-carboxamide;
96. 4-chloro-N-{5-[(4-methylpiperazin-1-yl)carbonyl]-1H-thieno[2,3-e]pyrazol-3-yl}benzamide;
97. 4-chloro-N-[5-(morpholin-4-ylcarbonyl)-1H-thieno[2,3-c]pyrazol-3-yl]benzamide;
98. 3-[(4-chlorobenzoyl)amino]-N-(2-morpholinylethyl)-1H-thieno[2,3-c]pyrazole-5-carboxamide;
99. 3-[(4-chlorobenzoyl)amino]-N-phenyl-1H-thieno[23]pyrazole-5-carboxamide;
100. 3-[(4-chlorobenzoyl)amino]-N-(2-methylphenyl)-1H-thieno[2,3-c]pyrazole-5-carboxamide;
101. 3-[(4-chlorobenzoyl)amino]-N-(4-cyanophenyl)-1H-thieno[2,3-c]pyrazole-5 carboxamide;
102. 3-[(4-chlorobenzoyl)amino]-N-fluorophenyl)-1H-thieno[2,3-c]pyrazole-5-carboxamide;
103. 3-[(4-chlorobenzoyl)amino]N-(4-chlorophenyl)-1H-thieno[2,3-c]pyrazole-5-carboxamide;
104. 3-[(4-chlorobenzoyl)amino]-N-(4-methoxyphenyl)-1H-thieno[2,3-c]pyrazole-5-carboxamide;
105. 3-[(4-chlorobenzoyl)amino]-N-(4-methylphenyl)-1H-thieno[2,3-c]pyrazole-5-carboxamide;
106. N-(tert-butyl)-3-[(4-chlorobenzoyl)amino]-1H-thieno[2,3-c]pyrazole-5-carboxamide;
107. 3-[(4-chlorobenzoyl)amino]-N-isopropyl-1H-thieno[2,3-c]pyrazole-5-carboxamide;
108. 3-[(4-chlorobenzoyl)amino]-N-ethyl-1H-thieno[2,3-c]pyrazole-5-carboxamide;
109. 4-methoxy-N-{5-[(4-methylpiperazin-1-yl)carbonyl]-1H-thieno[2,3-c]pyrazol-3-yl}benzamide;
110. 4-methoxy-N-[5-(morpholin-4-ylcarbonyl)-1H-thieno[2,3-c]pyrazol-3-yl]benzamide;
111. 3-[(4-methoxybenzoyl)amino]-N-(2-morpholin-4-ylethyl)-1H-thieno[2,3-c]pyrazole-5-carboxamide;
112. 3-[(4-methoxybenzoyl)amino]-N-phenyl-1H-thieno[2,3-c]pyrazole-5-carboxamide;
113. 3-[(4-methoxybenzoyl)amino]-N-(2-methylphenyl)-1H-thieno[2,3-c]pyrazole-5-carboxamide;
114. N-(4-cyanophenyl)-3-[(4-methoxybenzoyl)amino]-1H-thieno[2,3-c]pyrazole-5-carboxamide;

115. N-(4-fluorophenyl)-3-[(4-methoxybenzoyl)amino]-1H-thieno[2,3-c]pyrazole-5-carboxamide;
116. N-(4-chlorophenyl)-3-[(4-methoxybenzoyl)amino]-1H-thieno[2,3-c]pyrazole-5-carboxamide;
117. 3-[(4-methoxybenzoyl)amino]-N-(4-methoxyphenyl)-1H-thieno[2,3-c]pyrazole-5-carboxamide;
118. 3-[(4-methoxybenzoyl)amino]-N-(4-methylphenyl)-1H-thieno[2,3-c]pyrazole-5-carboxamide;
119. N-(tert-butyl)-3-[(4-methoxybenzoyl)amino]-1H-thieno[2,3-c]pyrazole-5-carboxamide;
120. N-isopropyl-3-[(4-methoxybenzoyl)amino]-1H-thieno[2,3-c]pyrazole-5-carboxamide;
121. N-ethyl-3-[(4-methoxybenzoyl)amino]-1H-thieno[2,3-c]pyrazole-5-carboxamide;
122. 4-tert-butyl-N-{5-[(4-methylpiperazin-1-yl)carbonyl]-1H-thieno[2,3-c]pyrazol-3-yl}benzamide;
123. 4-tert-butyl-N-[5-(morpholin-4-ylcarbonyl)-1H-thieno[2,3-c]pyrazol-3-yl]benzamide;
124. 3-[(4-tert-butylbenzoyl)amino]-N-(2-morpholin-4-ylethyl)1H-thieno[2,3-c]pyrazole-5-carboxamide;
125. 3-[(4-tert-butylbenzoyl)amino]-N-phenyl-1H-thieno[2,3-c]pyrazole-5-carboxamide;
126. 3-[(4-tert-butylbenzoyl)amino]-N-(2-methylphenyl)-1H-thieno[2,3-c]pyrazole-5-carboxamide;
127. 3-[(4-tert-butylbenzoyl)amino]-N-(4-cyanophenyl)-1H-thieno[2,3-c]pyrazole-5-carboxamide;
128. 3-[(4-tert-butylbenzoyl)amino]-N-(4-fluorophenyl)-1H-thieno[2,3-c]pyrazole-5-carboxamide;
129. 3-[(4-tert-butylbenzoyl)amino]-N-(4-chlorophenyl)-1H-thieno[2,3-c]pyrazole-5-carboxamide;
130. 3-[(4-tert-butylbenzoyl)amino]-N-(4-methoxyphenyl)-1H-thieno[2,3-c]pyrazole-5-carboxamide;
131. 3-[(4-tert-butylbenzoyl)amino]-N-(4-methylphenyl)-1H-thieno[2,3-c]pyrazole-5-carboxamide;
132. N-(tert-butyl)-3-[(4-tert-butylbenzoyl)amino]-1H-thieno[2,3-c]pyrazole-5-carboxamide;
133. 3-[(4-tert-butylbenzoyl)amino]-N-isopropyl-1H-thieno[2,3-c]pyrazole-5-carboxamide;
134. 3-[(4-tert-butylbenzoyl)amino]-N-ethyl-1H-thieno[2,3-c]pyrazol-5-carboxamide;
135. 4-methyl-N-{5-[(4-methylpiperazin-1-yl)carbonyl]-1H-thieno[2,3-c]pyrazol-3-yl}benzamide;
136. 4-methyl-N-[5-(morpholin-4-ylcarbonyl)-1H-thieno[2,3-c]pyrazol-3-yl]benzamide;
137. 3-[(4-methylbenzoyl)amino]-N-(2-morpholin-4-ylethyl)-1H-thieno[2,3-c]pyrazole-5-carboxamide;
138. 3-[(4-methylbenzoyl)amino]-N-phenyl-1H-thieno[2,3-c]pyrazole-5-carboxamide;
139. 3-[(4-methylbenzoyl)amino]-N-(2-methylphenyl)-1H-thieno[2,3-c]pyrazole-5-carboxamide;
140. N-(4-cyanophenyl)-3-[(4-methylbenzoyl)amino]-1H-thieno[2,3-c]pyrazole-5-carboxamide;
141. N-(4-fluorophenyl)-3-[(4-methylbenzoyl)amino]-1H-thieno[2,3-c]pyrazole-5-carboxamide;
142. N-(4-chlorophenyl)-3-[(4-methylbenzoyl)amino]-1H-thieno[2,3-c]pyrazole-5-carboxamide;
143. N-(4-methoxyphenyl)-3-[(4-methylbenzoyl)amino]-1H-thieno[2,3-c]pyrazole-5-carboxamide;
144. 3-[(4-methylbenzoyl)amino]-N-(4-methylphenyl)-1H-thieno[2,3-c]pyrazole-5-carboxamide;
145. N-(tert-butyl)-3-[(4-methylbenzoyl)amino]-1H-thieno[2,3-c]pyrazole-5-carboxamide;
146. N-isopropyl-3-[(4-methylbenzoyl)amino]-1H-thieno[2,3-c]pyrazole-5-carboxamide;
147. N-ethyl-3-[(4-methylbenzoyl)amino]-1H-thieno[2,3-c]pyrazole-5-carboxamide;
148. 3-[(3-fluorobenzoyl)amino]-N-(4-morpholin-4-ylphenyl)-1H-thieno[2,3-c]pyrazole-5-carboxamide;
149. N-(2-cyanophenyl)-3-[(3-fluorobenzoyl)amino]-1H-thieno[2,3-c]pyrazole-5-carboxamide;
150. 3-[(3-fluorobenzoyl)amino]-N-(2-fluorophenyl)-1H-thieno[2,3-c]pyrazole-5-carboxamide;
151. N-(2-chlorophenyl)-3-[(3-fluorobenzoyl)amino]-1H-thieno[2,3-c]pyrazol carboxamide;
152. N-(2,6-dichlorophenyl)3-[(3-fluorobenzoyl)amino]-1H-thieno[2,3-c]pyrazole-5-carboxamide;
153. 3-[(3-fluorobenzoyl)amino]-N-(2-methoxyphenyl)-1H-thieno[2,3-c]pyrazole-5-carboxamide;
154. N-(2,6-diethylphenyl)-3-[(3-fluorobenzoyl)amino]-1H-thieno[2,3-c]pyrazole-carboxamide;
155. N-(3-cyanophenyl)-3-[(3-fluorobenzoyl)amino]-1H-thieno[2,3-c]pyrazole-5-carboxamide;
156. 3-[(3-fluorobenzoyl)amino]-N-(3-fluorophenyl)-1H-thieno[2,3-c]pyrazole-5-carboxamide;
157. N-(3-chlorophenyl)-3-[(3-fluorobenzoyl)amino]-1H-thieno[2,3-c]pyrazole-5-carboxamide;
158. 3-[(3-fluorobenzoyl)amino]-N-(3-methoxyphenyl)-1H-thieno[2,3-c]pyrazole-5-carboxamide;
159. 3-[(3-fluorobenzoyl)amino]-N-(3-methylphenyl)-1H-thieno[2,3-c]pyrazole-5-carboxamide;
160. 3-[(3-fluorobenzoyl)amino]-N-[4-(4-methylpiperazin-1-yl)phenyl]-1H-thieno[2,3-c]pyrazole-5-carboxamide;
161. 3-[(3-chlorobenzoyl)amino]-N-(4-morpholin-4-ylphenyl)-1H-thieno[2,3-c]pyrazole-5-carboxamide;
162. 3-[(3-chlorobenzoyl)amino]-N-(2-cyanophenyl)-1H-thieno[2,3-c]pyrazole-5-carboxamide;
163. 3-[(3-chlorobenzoyl)amino]-N-2-fluorophenyl)-1H-thieno[2,3-c]pyrazole-5-carboxamide;
164. 3-[(3-chlorobenzoyl)amino]-N-(2-chlorophenyl)-1H-thieno[2,3-c]pyrazole-5-carboxamide;
165. 3-[(3-chlorobenzoyl)amino]-N-(2,6-dichlorophenyl)-1H-thieno[2,3-c]pyrazole-5-carboxamide;
166. 3-[(3-chlorobenzoyl)amino]-N-(2-methoxyphenyl)-1H-thieno[2,3-c]pyrazole-5-carboxamide;
167. 3-[(3-chlorobenzoyl)amino]-N-(2,6-diethylphenyl)-1H-thieno[2,3-c]pyrazole-5-carboxamide;
168. 3-[(3-chlorobenzoyl)amino]-N-(3-cyanophenyl)-1H-thieno[2,3-c]pyrazole-5-carboxamide;
169. 3-[(3-chlorobenzoyl)amino]-N-(3-fluorophenyl)-1H-thieno[2,3-e]pyrazole-5-carboxamide;
170. 3-[(3-chlorobenzoyl)amino]-N-(3-chlorophenyl)-1H-thieno[2,3-c]pyrazole-5-carboxamide;
171. 3-[(3-chlorobenzoyl)amino]-N-(3-methoxyphenyl)-1H-thieno[2,3-c]pyrazole-5-carboxamide;
172. 3-[(3-chlorobenzoyl)amino]-N-(3-methylphenyl)-1H-thieno[2,3-c]pyrazole-5-carboxamide;
173. 3-[(3-chlorobenzoyl)amino]-N-[4-(4-methylpiperazin-1-yl)phenyl]-1H-thieno[2,3-c]pyrazole-5-carboxamide;
174. 3-[(3-methoxybenzoyl)amino]-N-(4-morpholin-4-ylphenyl)-1H-thieno[2,3-c]pyrazole-5-carboxamide;
175. N-2-cyanophenyl)-3-[(3-methoxybenzoyl)amino]-1H-thieno[2,3-c]pyrazole-5-carboxamide;
176. N-(2-fluorophenyl)-3-[(3-methoxybenzoyl)amino]-1H-thieno[2,3-c]pyrazole-5-carboxamide;
177. N-2-chlorophenyl)-3-[(3-methoxybenzoyl)amino]-1H-thieno[2,3-c]pyrazole-5-carboxamide;
178. N-(2,6-dichlorophenyl)-3-[(3-methoxybenzoyl)amino]-1H-thieno[2,3-c]pyrazole-5-carboxamide;
179. 3-[(3-methoxybenzoyl)amino]-N-(2-methoxyphenyl)-1H-thieno[2,3-c]pyrazole-5-carboxamide;
180. N-(2,6-diethylphenyl)-3-[(3-methoxybenzoyl)amino]-1H-thieno[2,3-c]pyrazole-5-carboxamide;

181. N-(3-cyanophenyl)-3-[(3-methoxybenzoyl)amino]-1H-thieno[2,3-c]pyrazole-5-carboxamide;
182. N-(3-fluorophenyl)-3-[(3-methoxybenzoyl)amino]-1H-thieno[2,3-c]pyrazole-5-carboxamide;
183. N-(3-chlorophenyl)-3-[(3-methoxybenzoyl)amino]-1H-thieno[2,3-c]pyrazole-5-carboxamide;
184. 3-[(3-methoxybenzoyl)amino]-N-(3-methoxyphenyl)-1H-thieno[2,3-c]pyrazole-5-carboxamide;
185. 3-[(3-methoxybenzoyl)amino]-N-(3-methylphenyl)-1H-thieno[2,3-c]pyrazole-5-carboxamide;
186. 3-[(3-methoxybenzoyl)amino]-N-[4-(4-methylpiperazin-1-yl)phenyl]-1H-thieno[2,3-c]pyrazole-5-carboxamide;
187. N-(4-morpholin-4-ylphenyl)-3-[(phenylacetyl)amino]-1H-thieno[2,3-c]pyrazole-5-carboxamide;
188. N-(2-cyanophenyl)-3-[(phenylacetyl)amino]-1H-thieno[2,3-c]pyrazole-5-carboxamide;
189. N-(2-fluorophenyl)-3-[(phenylacetyl)amino]-1H-thieno[2,3-c]pyrazole-5-carboxamide;
190. N-(2-chlorophenyl)-3-[(phenylacetyl)amino]-1H-thieno[2,3-c]pyrazole-5-carboxamide;
191. N-(2,6-dichlorophenyl)-3-[(phenylacetyl)amino]-1H-thieno[2,3-c]pyrazole-5-carboxamide;
192. N-(2-methoxyphenyl)-3-[(phenylacetyl)amino]-1H-thieno[2,3-c]pyrazole-5-carboxamide;
193. N-(2,6-diethylphenyl)-3-[(phenylacetyl)amino]-1H-thieno[2,3-c]pyrazole-5-carboxamide;
194. N-(3-cyanophenyl)-3-[(phenylacetyl)amino]-1H-thieno[2,3-c]pyrazole-5-carboxamide;
195. N-(3-fluorophenyl)-3-[(phenylacetyl)amino]-1H-thieno[2,3-c]pyrazole-5-carboxamide;
196. N-(3-chlorophenyl)-3-[(phenylacetyl)amino]-1H-thieno[2,3-c]pyrazole-5-carboxamide;
197. N-(3-methoxyphenyl)-3-[(phenylacetyl)amino]-1H-thieno[2,3-c]pyrazole-5-carboxamide;
198. N-(3-methylphenyl)-3-[(phenylacetyl)amino]-1H-thieno[2,3-c]pyrazole-5-carboxamide;
199. N-[4-(4-methylpiperazin-1-yl)phenyl]-3-[(phenylacetyl)amino]-1H-thieno[2,3-c]pyrazole-5-carboxamide;
200. 3-{[(2-fluorophenyl)acetyl]amino}-N-(4-morpholin-4-ylphenyl)-1H-thieno[2,3-c]pyrazole-5-carboxamide;
201. N-2-cyanophenyl)-3-{[(2-fluorophenyl)acetyl]amino}-1H-thieno[2,3-c]pyrazole-5-carboxamide;
202. N-(2-fluorophenyl)-3-{[(2-fluorophenyl)acetyl]amino}-1H-thieno[2,3-c]pyrazole-5-carboxamide;
203. N-(2-chlorophenyl)-3-{[(2-fluorophenyl)acetyl]amino}-1H-thieno[2,3-c]pyrazole-5-carboxamide;
204. N-(2,6-dichlorophenyl)-3-{[(2-fluorophenyl)acetyl]amino}-1H-thieno[2,3-c]pyrazole-5-carboxamide;
205. 3-{[(2-fluorophenyl)acetyl]amino}-N-(2-methoxyphenyl)-1H-thieno[2,3-c]pyrazole-5 carboxamide;
206. N-(2,6-diethylphenyl)-3-{[(2-fluorophenyl)acetyl]amino}-1H-thieno[2,3-c]pyrazole-5-carboxamide;
207. N-(3 cyanophenyl)-3-{[(2-fluorophenyl)acetyl]amino}-1H-thieno[2,3-c]pyrazole-5-carboxamide;
208. N-(3-fluorophenyl)-3-{[(2-fluorophenyl)acetyl]amino}-1H-thieno[2,3-c]pyrazole-5-carboxamide;
209. N-(3-chlorophenyl)-3-{[(2-fluorophenyl)acetyl]amino}-1H-thieno[2,3-c]pyrazole-5-carboxamide;
210. 3-{[(2-fluorophenyl)acetyl]amino}-N-(3-methoxyphenyl)-1H-thieno[2,3-c]pyrazole-5-carboxamide;
211. 3-{[(2-fluorophenyl)acetyl]amino}-N-(3-methylphenyl)-1H-thieno[2,3-c]pyrazole-5-carboxamide;
212. 3-{[(2-fluorophenyl)acetyl]amino}-N-[4(4-methylpiperazin-1-yl)phenyl]-1H-thieno[2,3-c]pyrazole-5-carboxamide;
213. 3-{[(2-methylphenyl)acetyl]amino}-N-(4-morpholin-4-ylphenyl)-1H-thieno[2,3-c]pyrazole-5-carboxamide;
214. N-(2-cyanophenyl)-3-{[(2-methylphenyl)acetyl]amino}-1H-thieno[2,3-c]pyrazole-5-carboxamide;
215. N-(2-fluorophenyl)-3-{[(2-methylphenyl)acetyl]amino}-1H-thieno[2,3-c]pyrazole-5-carboxamide;
216. N-(2-chlorophenyl)-3-{[(2-methylphenyl)acetyl]amino}-1H-thieno[2,3-c]pyrazole-5-carboxamide;
217. N-(2,6-dichlorophenyl)-3-{[(2-methylphenyl)acetyl]amino}-1H-thieno[2,3-c]pyrazole-5-carboxamide;
218. N-(2-methoxyphenyl)-3-{[(2-methylphenyl)acetyl]amino}-1H-thieno[2,3-c]pyrazole-5-carboxamide;
219. N-(2,6-diethylphenyl)-3-{[(2-methylphenyl)acetyl]amino}-1H-thieno[2,3-c]pyrazole-5-carboxamide;
220. N-(3 cyanophenyl)-3-{[(2-methylphenyl)acetyl]amino}-1H-thieno[2,3-c]pyrazole-5-carboxamide;
221. N-(3-fluorophenyl)-3-{[(2-methylphenyl)acetyl]amino}-1H-thieno[2,3-c]pyrazole-5-carboxamide;
222. N-(3-chlorophenyl)-3-{[(2-methylphenyl)acetyl]amino}-1H-thieno[2,3-c]pyrazole-5-carboxamide;
223. N-(3-methoxyphenyl)-3-{[(2-methylphenyl)acetyl]amino}-1H-thieno[2,3-c]pyrazole-5-carboxamide;
224. N-(3-methylphenyl)-3-{[(2-methylphenyl)acetyl]amino}-1H-thieno[2,3-c]pyrazole-5-carboxamide;
225. 3-{[(2-methylphenyl)acetyl]amino}-N-[4-(4-methylpiperazin-1-yl)phenyl]-1H-thieno[2,3-c]pyrazole-5-carboxamide;
226. 3-{[(4-fluorophenyl)acetyl]amino}-N-(4-morpholin-4-ylphenyl)-1H-thieno[2,3-c]pyrazole-5-carboxamide;
227. N-2-cyanophenyl)-3-{[(4-fluorophenyl)acetyl]amino}-1H-thieno[2,3-c]pyrazole-5-carboxamide;
228. N-(2-fluorophenyl)-3-{[(4-fluorophenyl)acetyl]amino}-1H-thieno[2,3-c]pyrazole-5-carboxamide;
229. N-(2-chlorophenyl)-3-{([(4-fluorophenyl)acetyl]amino}-1H-thieno[2,3-c]pyrazole-5-carboxamide;
230. N-(2,6-dichlorophenyl)-3-{[(4-fluorophenyl)acetyl]amino}-1H-thieno[2,3-c]pyrazole-5-carboxamide;
231. 3-{[(4-fluorophenyl)acetyl]amino}-N-(2-methoxyphenyl)-1H-thieno[2,3-c]pyrazole-5-carboxamide;
232. N-(2,6-diethylphenyl)-3-{[(4-fluorophenyl)acetyl]amino}-1H-thieno[2,3-c]pyrazole-5-carboxamide
233. N-(3-cyanophenyl)-3-{[(4-fluorophenyl)acetyl]amino}-1H-thieno[2,3-c]pyrazole-5-carboxamide;
234. N-(3-fluorophenyl)-3-{[(4-fluorophenyl)acetyl]amino}-1H-thieno[2,3-c]pyrazole-5-carboxamide;
235. N-(3-chlorophenyl)-3-{[(4-fluorophenyl)acetyl]amino}-1H-thieno[2,3-c]pyrazole-5-carboxamide;
236. 3-{[(4-fluorophenyl)acetyl]amino}-N-(3-methoxyphenyl)-1H-thieno[2,3-c]pyrazole-5-carboxamide;
237. 3-{[(4-fluorophenyl)acetyl]amino}-N-(3-methylphenyl)-1H-thieno[2,3-c]pyrazole-5-carboxamide;
238. 3-{[(4-fluorophenyl)acetyl]amino}-N-[4-(4-methylpiperazin-1-yl)phenyl]-1H-thieno[2,3-c]pyrazole-5-carboxamide;
239. 3-{[(4-chlorophenyl)acetyl]amino}-N-(4 morpholin-4-ylphenyl)-1H-thieno[2,3-c]pyrazole-5-carboxamide;
240. 3-{[(4-chlorophenyl)acetyl]amino}-N-(2-cyanophenyl)-1H-thieno[2,3-c]pyrazole-5-carboxamide;
241. 3-{[(4-chlorophenyl)acetyl]amino}-N-(2-fluorophenyl)-1H-thieno[2,3-c]pyrazole-5-carboxamide;
242. N-2-chlorophenyl)-3-{[(4-chlorophenyl)acetyl]amino}-1H-thieno[2,3-c]pyrazole-5-carboxamide;
243. 3-{[(4-chlorophenyl)acetyl]amino}-N-(2,6-dichlorophenyl)-1H-thieno[2,3-c]pyrazole-5-carboxamide;
244. 3-{[(4-chlorophenyl)acetyl]amino}-N-(2-methoxyphenyl)-1H-thieno[2,3-c]pyrazole-5-carboxamide;

245. 3-{[(4-chlorophenyl)acetyl]amino}-N-(2,6-diethylphenyl)-1H-thieno[2,3-c]pyrazole-5-carboxamide;
246. 3-{[(4-chlorophenyl)acetyl]amino}-N-(3-cyanophenyl)-1H-thieno[2,3-c]pyrazole-5-carboxamide;
247. 3-{[(4-chlorophenyl)acetyl]amino}-N-(3-fluorophenyl)-1H-thieno[2,3-c]pyrazole-5-carboxamide;
248. N-(3-chlorophenyl)-3-{[(4-chlorophenyl)acetyl]amino}-1H-thieno[2,3-c]pyrazole-5-carboxamide;
249. 3-{[(4-chlorophenyl)acetyl]amino}-N-(3-methoxyphenyl)-1H-thieno[2,3-c]pyrazole-5-carboxamide;
250. 3-{[(4-chlorophenyl)acetyl]amino}-N-(3-methylphenyl)-1H-thieno[2,3-c]pyrazole-5-carboxamide;
251. 3-{[(4-chlorophenyl)acetyl]amino}-N-[4-(4-methylpiperazin-1-yl)phenyl]-1H-thieno[2,3-c]pyrazole-5-carboxamide;
252. 3-{[(4-methoxyphenyl)acetyl]amino}-N-(4-morpholin-4-ylphenyl)-1H-thieno[2,3-c]pyrazole-5-carboxamide;
253. N-(2-cyanophenyl)-3-{[(4-methoxyphenyl)acetyl]amino}-1H-thieno[2,3-c]pyrazole-5-carboxamide;
254. N-(2-fluorophenyl)-3-{[(4-methoxyphenyl)acetyl]amino}-1H-thieno[2,3-c]pyrazole-5-carboxamide;
255. N-(2-chlorophenyl)-3-{[(4-methoxyphenyl)acetyl]amino}-1H-thieno[2,3-c]pyrazole-5-carboxamide;
256. N-(2,6-dichlorophenyl)-3-{[(4-methoxyphenyl)acetyl]amino}-1H-thieno[2,3-c]pyrazole-5-carboxamide;
257. N-(2-methoxyphenyl)-3-{[(4-methoxyphenyl)acetyl]amino}-1H-thieno[2,3-c]pyrazole-5-carboxamide;
258. N-(2,6-diethylphenyl)-3-{[(4-methoxyphenyl)acetyl]amino}-1H-thieno[2,3-c]pyrazole-5-carboxamide;
259. N-(3-cyanophenyl)-3-{[(4-methoxyphenyl)acetyl]amino}-1H-thieno[2,3-c]pyrazole-5-carboxamide;
260. N-(3-fluorophenyl)-3-{[(4-methoxyphenyl)acetyl]amino}-1H-thieno[2,3-c]pyrazole-5-carboxamide;
261. N-(3-chlorophenyl)-3-{[(4-methoxyphenyl)acetyl]amino}-1H-thieno[2,3-c]pyrazole-5-carboxamide;
262. N-(3-methoxyphenyl)-3-{[(4-methoxyphenyl)acetyl]amino}-1H-thieno[2,3-c]pyrazole-5-carboxamide;
263. 3-{[(4-methoxyphenyl)acetyl]amino}-N-(3-methylphenyl)-1H-thieno[2,3-c]pyrazole-5-carboxamide;
264. 3-{[(4-methoxyphenyl)acetyl]amino}-N-[4-(4-methylpiperazin-1-yl)phenyl]-1H-thieno[2,3-c]pyrazole-5-carboxamide;
265. 3-{[(4-methylphenyl)acetyl]amino}-N-(4-morpholin-4-ylphenyl)-1H-thieno[2,3-c]pyrazole-5-carboxamide;
266. N-(2-cyanophenyl)-3-{[(4-methylphenyl)acetyl]amino}-1H-thieno[2,3-c]pyrazole-5-carboxamide;
267. N-(2-fluorophenyl)-3-{[(4-methylphenyl)acetyl]amino}-1H-thieno[2,3-c]pyrazole-5-carboxamide;
268. N-(2-chlorophenyl)-3-{[(4-methylphenyl)acetyl]amino}-1H-thieno[2,3-c]pyrazole-5-carboxamide;
269. N-(2,6-dichlorophenyl)-3-{[(4-methylphenyl)acetyl]amino}-1H-thieno[2,3-c]pyrazole-5-carboxamide;
270. N-(2-methoxyphenyl-3-{[(4-methylphenyl)acetyl]amino}-1H-thieno[2,3-c]pyrazole-5-carboxamide;
271. N-(2,6-diethylphenyl)-3-{[(4-methylphenyl)acetyl]amino}-1H-thieno[2,3-c]pyrazole-5-carboxamide;
272. N-(3-cyanophenyl)-3-{[(4-methylphenyl)acetyl]amino}-1H-thieno[2,3-c]pyrazole-5-carboxamide;
273. N-(3-fluorophenyl)-3-{[(4-methylphenyl)acetyl]amino}-1H-thieno[2,3-c]pyrazole-5-carboxamide;
274. N-(3-chlorophenyl)-3-{[(4-methylphenyl)acetyl]amino}-1H-thieno[2,3-c]pyrazole-5-carboxamide;
275. N-(3-methoxyphenyl)-3-{[(4-methylphenyl)acetyl]amino}-1H-thieno[2,3-c]pyrazole-5-carboxamide;
276. N-(3-methylphenyl)-3-{[(4-methylphenyl)acetyl]amino}-1H-thieno[2,3-c]pyrazole-5-carboxamide;
277. 3-{[(4-methylphenyl)acetyl]amino}-N-[4-(4-methylpiperazin-1-yl)phenyl]-1H-thieno[2,3-c]pyrazole-5-carboxamide;
278. 3-{[(4-tert-butylphenyl)acetyl]amino}-N-(4-morpholin-4-ylphenyl)-1H-thieno[2,3-c]pyrazole-5-carboxamide;
279. 3-{[(4-tert-butylphenyl)acetyl]amino}-N-(2-cyanophenyl)-1H-thieno[2,3-c]pyrazole-carboxamide;
280. 3-{[(4-tert-butylphenyl)acetyl]amino}-N-2-fluorophenyl)-1H-thieno[2,3-c]pyrazole-5-carboxamide;
281. 3-{[(4-tert-butylphenyl)acetyl]amino}-N-(2-chlorophenyl)-1H-thieno[2,3-c]pyrazole-5-carboxamide;
282. 3-{[(4-tert-butylphenyl)acetyl]amino}-N-(2,6-dichlorophenyl)-1H-thieno[2,3-c]pyrazole-5-carboxamide;
283. 3-{[(4-tert-butylphenyl)acetyl]amino}-N-(2-methoxyphenyl)-1H-thieno[2,3-c]pyrazole-5-carboxamide;
284. 3-{[(4-tert-butylphenyl)acetyl]amino}-N-(2,6-diethylphenyl)-1H-thieno[2,3-c]pyrazole-5-carboxamide;
285. 3-{[(4-tert-butylphenyl)acetyl]amino}-N-(3-cyanophenyl)-1H-thieno[2,3-c]pyrazole-5-carboxamide;
286. 3-{[(4-tert-butylphenyl)acetyl]amino}-N-(3-fluorophenyl)-1H-thieno[2,3-c]pyrazole-5-carboxamide;
287. 3-{[(4-tert-butylphenyl)acetyl]amino}-N-(3-chlorophenyl)-1H-thieno[2,3-c]pyrazole-5-carboxamide;
288. 3-{[(4 tert-butylphenyl)acetyl]amino}-N-(3-methoxyphenyl)-1H-thieno[2,3-c]pyrazole-5-carboxamide;
289. 3-{[(4-tert-butylphenyl)acetyl]amino}-N-(3-methylphenyl)-1H-thieno[2,3-c]pyrazole-5-carboxamide;
290. 3-{[(4-tert-butylphenyl)acetyl]amino}-N-[4-(4-methylpiperazin-1-yl)phenyl]-1H-thieno[2,3-c]pyrazole-5-carboxamide;
291. N-benzyl-3-{[(2-chlorophenyl)acetyl]amino}-1H-thieno[2,3-c]pyrazole-5-carboxamide;
292. 3-{[(2-chlorophenyl)acetyl]amino}-N-(2-fluorobenzyl)-1H-thieno[2,3-c]pyrazole-5-carboxamide;
293. N-2-chlorobenzyl-3-{[(2-chlorophenyl)acetyl]amino}-1H-thieno[2,3-c]pyrazole-5-carboxamide;
294. 3-{[(2-chlorophenyl)acetyl]amino}-N-(2-methoxybenzyl)-1H-thieno[2,3-c]pyrazole-5-carboxamide;
295. 3-{[(2-chlorophenyl)acetyl]amino}N-(2-methylbenzyl)-1H-thieno[2,3-c]pyrazole-5-carboxamide;
296. 3-{[(2-chlorophenyl)acetyl]amino}-N-(3-fluorobenzyl)-1H-thieno[2,3-c]pyrazole-5-carboxamide;
297. 3-{[(2-chlorophenyl)acetyl]amino}-N-(3-methoxybenzyl)-1H-thieno[2,3-c]pyrazole-5-carboxamide;
298. 3-{[(2-chlorophenyl)acetyl]amino}-N-(3-methylbenzyl)-1H-thieno[2,3-c]pyrazole-5-carboxamide;
299. 3-{[(2-chlorophenyl)acetyl]amino}-N-(4-fluorobenzyl)-1H-thieno[2,3-c]pyrazole-5-carboxamide;
300. N-(4-chlorobenzyl)-3-{[(2-chlorophenyl)acetyl]amino}-1H-thieno[2,3-c]pyrazole-5-carboxamide;
301. 3-{[(2-chlorophenyl)acetyl]amino}-N-(4-methoxybenzyl)-1H-thieno[2,3-c]pyrazole-5-carboxamide;
302. 3-{([(2-chlorophenyl)acetyl]amino}-N-(4-methylbenzyl)-1H-thieno[2,3-c]pyrazol-5-carboxamide;
303. N-(3-chlorobenzyl)-3-{[(2-chlorophenyl)acetyl]amino}-1H-thieno[2,3-c]pyrazole-5-carboxamide;
304. N-benzyl-3-{[(2-methoxyphenyl)acetyl]amino}-1H-thieno[2,3-c]pyrazole-5-carboxamide;

305. N-2-fluorobenzyl-3-{[(2-methoxyphenyl)acetyl] amino}-1H-thieno[2,3-c]pyrazole-5-carboxamide;
306. N-2-chlorobenzyl-3-{[(2-methoxyphenyl)acetyl] amino}-1H-thieno[2,3-c]pyrazole-5-carboxamide;
307. N-(2-methoxybenzyl)-3-{[(2-methoxyphenyl) acetyl]amino}-1H-thieno[2,3-c]pyrazole-5-carboxamide;
308. 3-{[(2-methoxyphenyl)acetyl]amino}-N-(2-methylbenzyl)-1H-thieno[2,3-c]pyrazole-5-carboxamide;
309. N-(3-fluorobenzyl)-3-{([(2-methoxyphenyl)acetyl] amino}-1H-thieno[2,3-c]pyrazole-5-carboxamide;
310. N-(3-methoxybenzyl)-3-{[(2-methoxyphenyl) acetyl]amino}-1H-thieno[2,3-c]pyrazol-5-carboxamide;
311. 3-{[(2-methoxyphenyl)acetyl]amino}-N-(3-methylbenzyl)-1H-thieno[2,3-c]pyrazole-5-carboxamide;
312. N-(4-fluorobenzyl)-3-{[(2-methoxyphenyl)acetyl] amino}-1H-thieno[2,3-c]pyrazole-5-carboxamide;
313. N-(4-chlorobenzyl)-3-{[(2-methoxyphenyl)acetyl] amino}-1H-thieno[2,3-c]pyrazole-5 carboxamide;
314. N-(4-methoxybenzyl)-3-{[(2-methoxyphenyl) acetyl]amino}-1H-thieno[2,3-c]pyrazole-5-carboxamide;
315. 3-{[(2-methoxyphenyl)acetyl]amino}-N-(4-methylbenzyl)-1H-thieno[2,3-c]pyrazole-5-carboxamide;
316. N-(3-chlorobenzyl)-3-{[(2-methoxyphenyl)acetyl] amino}-1H-thieno[2,3-c]pyrazole-5-carboxamide;
317. N-benzyl-3-{[(3-fluorophenyl)acetyl]amino}-1H-thieno[2,3-c]pyrazole-5-carboxamide;
318. N-2-fluorobenzyl-3-{[(3-fluorophenyl)acetyl] amino}-1H-thieno[2,3-c]pyrazole-5-carboxamide;
319. N-2-chlorobenzyl-3-{[(3-fluorophenyl)acetyl] amino}-1H-thieno[2,3-c]pyrazole-5-carboxamide;
320. 3-{[(3-fluorophenyl)acetyl]amino}-N-(2-methoxybenzyl)-1H-thieno[2,3-c]pyrazole-5-carboxamide;
321. 3-{[(3-fluorophenyl)acetyl]amino}-N-(2-methylbenzyl)-1H-thieno[2,3-c]pyrazole-5-carboxamide;
322. N-(3-fluorobenzyl)-3-{[(3-fluorophenyl)acetyl] amino}-1H-thieno[2,3-c]pyrazole-5-carboxamide;
323. 3-{[(3-fluorophenyl)acetyl]amino}-N-(3-methoxybenzyl)-1H-thieno[2,3-c]pyrazole-5-carboxamide;
324. 3-{[(3-fluorophenyl)acetyl]amino}-N-(3-methylbenzyl)-1H-thieno[2,3-c]pyrazole-5-carboxamide;
325. N-(4-fluorobenzyl)-3-{[(3-fluorophenyl)acetyl] amino}-1H-thieno[2,3-c]pyrazole-5-carboxamide;
326. N-(4-chlorobenzyl)-3-{[(3-fluorophenyl)acetyl] amino}-1H-thieno[2,3-c]pyrazole-5-carboxamide;
327. 3-{[(3-fluorophenyl)acetyl]amino}-N-(4-methoxybenzyl)-1H-thieno[2,3-c]pyrazole-5 carboxamide;
328. 3-{[(3-fluorophenyl)acetyl]amino}-N-(4-methylbenzyl)-1H-thieno[2,3-c]pyrazole-5-carboxamide;
329. N-(3-chlorobenzyl)-3-{[(3-fluorophenyl)acetyl] amino}-1H-thieno[2,3-c]pyrazole-5-carboxamide,
330. N-benzyl-3-{[(3-chlorophenyl)acetyl]amino}-1H-thieno[2,3-c]pyrazole-5-carboxamide;
331. 3-{[(3-chlorophenyl)acetyl]amino}-N-2-fluorobenzyl)-1H-thieno[2,3-c]pyrazole-5-carboxamide;
332. N-(2-chlorobenzyl)-3-{[(3-chlorophenyl)acetyl] amino}-1H-thieno[2,3-c]pyrazole-5-carboxamide;
333. 3-{[(3-chlorophenyl)acetyl]amino}-N-(2-methoxybenzyl)-1H-thieno[2,3-c]pyrazole-5-carboxamide;
334. 3-{[(3 chlorophenyl)acetyl]amino}-N-(2-methylbenzyl)-1H-thieno[2,3-c]pyrazole-5-carboxamide;
335. 3-{[(3-chlorophenyl)acetyl]amino}-N-(3-fluorobenzyl)-1H-thieno[2,3-c]pyrazole-5-carboxamide;
336. 3-{[(3-chlorophenyl)acetyl]amino}-N-(3-methoxybenzyl)-1H-thieno[2,3-c]pyrazole-5-carboxamide;
337. 3-{[3-chlorophenyl)acetyl]amino}-N-(3-methylbenzyl)-1H-thieno[2,3-c]pyrazole-5-carboxamide;
338. 3-{[(3-chlorophenyl)acetyl]amino})-N-fluorobenzyl)-1H-thieno[2,3-c]pyrazole-5-carboxamide;
339. N-(4-chlorobenzyl)-3-{[(3-chlorophenyl)acetyl] amino}-1H-thieno[2,3-c]pyrazole-5-carboxamide;
340. 3-{[(3-chlorophenyl)acetyl]amino}-N-(4-methoxybenzyl)-1H-thieno[2,3-c]pyrazole-5-carboxamide;
341. 3-{[(3-chlorophenyl)acetyl]amino}-N-(4-methylbenzyl)-1H-thieno[2,3-c]pyrazole-5-carboxamide;
342. N-(3-chlorobenzyl)-3-{[(3-chlorophenyl)acetyl] amino}-1H-thieno[2,3-c]pyrazole-5-carboxamide;
343. N-benzyl-3-{[(3-methoxyphenyl)acetyl]amino}-1H-thieno[2,3-c]pyrazole-5-carboxamide;
344. N-(2-fluorobenzyl)-3-{[(3-methoxyphenyl)acetyl] amino}-1H-thieno[2,3-c]pyrazole-5-carboxamide;
345. N-(2-chlorobenzyl)-3-{[(3-methoxyphenyl)acetyl] amino}-1H-thieno[2,3-c]pyrazole-5-carboxamide;
346. N-(2-methoxybenzyl)-3-{[(3-methoxyphenyl) acetyl]amino}-1H-thieno[2,3-c]pyrazole-5-carboxamide;
347. 3-{[(3-methoxyphenyl)acetyl]amino}-N-(2-methylbenzyl)-1H-thieno[2,3-c]pyrazole-5-carboxamide;
348. N-(3-fluorobenzyl)-3-{[(3-methoxyphenyl)acetyl] amino}-1H-thieno[2,3-c]pyrazole-5-carboxamide;
349. N-(3-methoxybenzyl)-3-{[(3-methoxyphenyl) acetyl]amino}-1H-thieno[2,3-c]pyrazole-5-carboxamide;
350. 3-{[(3-methoxyphenyl)acetyl]amino}-N-(3-methylbenzyl)-1H-thieno[2,3-c]pyrazole-5-carboxamide;
351. N-(4-fluorobenzyl)-3-{[(3-methoxyphenyl)acetyl] amino}-1H-thieno[2,3-c]pyrazole-5-carboxamide;
352. N-(4-chlorobenzyl)-3-{[(3-methoxyphenyl)acetyl] amino}-1H-thieno[2,3-c]pyrazole-5-carboxamide;
353. N-(4-methoxybenzyl)-3-{[(3-methoxyphenyl) acetyl]amino}-1H-thieno[2,3-c]pyrazole-5-carboxamide;
354. 3-{[(3-methoxyphenyl)acetyl]amino}-N-(4-methylbenzyl)-1H-thieno[2,3-c]pyrazole-5-carboxamide;
355. N-(3-chlorobenzyl)-3-{[(3-methoxyphenyl)acetyl] amino}-1H-thieno[2,3-c]pyrazole-5-carboxamide;
356. N-benzyl-3-{[(3-methylphenyl)acetyl]amino}-1H-thieno[2,3-c]pyrazole-5-carboxamide;
357. N-2-fluorobenzyl-3-{[(3-methylphenyl)acetyl] amino}-1H-thieno[2,3-c]pyrazole-5-carboxamide;
358. N-(2-chlorobenzyl)-3-{[(3-methylphenyl)acetyl] amino}-1H-thieno[2,3-c]pyrazole-5-carboxamide;
359. N-(2-methoxybenzyl)-3-{[(3-methylphenyl)acetyl] amino}-1H-thieno[2,3-c]pyrazole-5-carboxamide;
360. N-(2-methylbenzyl)-3-{[(3-methylphenyl)acetyl] amino}-1H-thieno[2,3-c]pyrazole-5-carboxamide;
361. N-(3-fluorobenzyl)-3-{[(3-methylphenyl)acetyl] amino}-1H-thieno[2,3-c]pyrazole-5-carboxamide;
362. N-(3-methoxybenzyl)-3-{[(3-methylphenyl)acetyl] amino}-1H-thieno[2,3-c]pyrazole-5-carboxamide;
363. N-(3-methylbenzyl)-3-{[(3-methylphenyl)acetyl] amino}-1H-thieno[2,3-c]pyrazole-5-carboxamide;
364. N-(4-fluorobenzyl)-3-{[(3-methylphenyl)acetyl] amino}-1H-thieno[2,3-c]pyrazol-5-carboxamide;
365. N-(chlorobenzyl)-3-{[(3-methylphenyl)acetyl] amino}-1H-thieno[2,3-c]pyrazole-5 carboxamide;
366. N-(4 methoxybenzyl)-3-{[(3-methylphenyl)acetyl] amino}-1H-thieno[2,3-c]pyrazole-5-carboxamide;
367. N-(4-methylbenzyl)-3-{[(3-methylphenyl)acetyl] amino}-1H-thieno[2,3-c]pyrazole-5-carboxamide;
368. N-(3-chlorobenzyl)-3-{[(3-methylphenyl)acetyl] amino}-1H-thieno[2,3-c]pyrazole-5-carboxamide, 369. N-benzyl-3-[(thien-2-ylcarbonyl)amino]-1H-thieno[2,3-c]pyrazole-5-carboxamide;
370. N-(2-fluorobenzyl)-3-[(thien-2-ylcarbonyl)amino]-1H-thieno[2,3-c]pyrazole-5-carboxamide;
371. N-2-chlorobenzyl)-3-[(thien-2-ylcarbonyl)amino]-1H-thieno[2,3-c]pyrazole-5-carboxamide;
372. N-(2-methoxybenzyl)-3-[(thien-2-ylcarbonyl)amino]-1H-thieno[2,3-c]pyrazole-5-carboxamide;
373. N-(2-methylbenzyl)-3-[(thien-2-ylcarbonyl)amino]-1H-thieno[2,3-c]pyrazole-5-carboxamide;
374. N-(3-fluorobenzyl)-3-[(thien-2-ylcarbonyl)amino]-1H-thieno[2,3-c]pyrazole-5-carboxamide;
375. N-(3-methoxybenzyl)-3-[(thien-2-ylcarbonyl)amino]-1H-thieno[2,3-c]pyrazole-5-carboxamide;
376. N-(3-methylbenzyl)-3-[(thien-2-ylcarbonyl)amino]-1H-thieno[2,3-c]pyrazole-5-carboxamide;
377. N-(4-fluorobenzyl)-3-[(thien-2-ylcarbonyl)amino]-1H-thieno[2,3-c]pyrazole-5-carboxamide;
378. N-(4-chlorobenzyl)-3-[(thien-2-ylcarbonyl)amino]-1H-thieno[2,3-c]pyrazole-5-carboxamide;
379. N-(4-methoxybenzyl)-3-[(thien-2-ylcarbonyl)amino]-1H-thieno[2,3-c]pyrazole-5-carboxamide;
380. N-(4-methylbenzyl)-3-[(thien-2-ylcarbonyl)amino]-1H-thieno[2,3-c]pyrazole-5-carboxamide;
381. N-(3-chlorobenzyl)-3-[(thien-2-ylcarbonyl)amino]-1H-thieno[2,3-c]pyrazole-5-carboxamide;
382. N-benzyl-3-(isonicotinoylamino)-1H-thieno[2,3-c]pyrazole-5-carboxamide;
383. N-(2-fluorobenzyl)-3-(isonicotinoylamino)-1H-thieno[2,3-c]pyrazole-5-carboxamide;
384. N-(2-chlorobenzyl)-3-(isonicotinoylamino)-1H-thieno[2,3-c]pyrazole-5-carboxamide;
385. 3-(isonicotinoylamino)-N-(2-methoxybenzyl)-1H-thieno[2,3-c]pyrazole-5-carboxamide;
386. 3-isonicotinoylamino)-N-(2-methylbenzyl)-1H-thieno[2,3-c]pyrazole-5-carboxamide;
387. N-(3-fluorobenzyl)-3-(isonicotinoylamino)-1H-thieno[2,3-c]pyrazole-5-carboxamide;
388. 3-(isonicotinoylamino)-N-(3-methoxybenzyl)-1H-thieno[2,3-c]pyrazole-5-carboxamide;
389. 3-(isonicotinoylamino)-N-(3-methylbenzyl)-1H-thieno[2,3-c]pyrazole-5-carboxamide;
390. N-(4-fluorobenzyl)-3-(isonicotinoylamino)-1H-thieno[2,3-c]pyrazole-5-carboxamide;
391. N-(4 chlorobenzyl)-3-(isonicotinoylamino)-1H-thieno[2,3]pyrazole-5-carboxamide;
392. 3-isonicotinoylamino)-N-(4-methoxybenzyl)-1H-thieno[2,3-c]pyrazole-5-carboxamide;
393. 3-(isonicotinoylamino)-N-(4-methylbenzyl)-1H-thieno[2,3-c]pyrazole-5-carboxamide;
394. N-(3-chlorobenzyl)-3-(isonicotinoylamino)-1H-thieno[2,3-c]pyrazole-5-carboxamide;
395. N-benzyl-3-[(1,3-thiazol-2-ylcarbonyl)amino]-1H-thieno[2,3-c]pyrazole-5-carboxamide;
396. N-(2-fluorobenzyl)-3-[(1,3-thiazol-2-ylcarbonyl)amino]-1H-thieno[2,3-c]pyrazole-5-carboxamide;
397. N-(2-chlorobenzyl)-3-[(1,3-thiazol-2-ylcarbonyl)amino]-1H-thieno[2,3-c]pyrazole-5-carboxamide;
398. N-(2-methoxybenzyl)-3-[(1,3-thiazol-2-ylcarbonyl)amino]-1H-thieno[2,3-c]pyrazole-5-carboxamide;
399. N-(2-methylbenzyl)-3-[(1,3-thiazol-2-ylcarbonyl)amino]-1H-thieno[2,3-c]pyrazole-5 carboxamide;
400. N-(3-fluorobenzyl)-3-[(1,3-thiazol-2-ylcarbonyl)amino]-1H-thieno[2,3-c]pyrazole-5-carboxamide;
401. N-(3-methoxybenzyl)-3-[(1,3-thiazol-2-ylcarbonyl)amino]-1H-thieno[2,3-c]pyrazole-5-carboxamide;
402. N-(3-methylbenzyl)-3-[(1,3-thiazol-2-ylcarbonyl)amino]-1H-thieno[2,3-c]pyrazole-5-carboxamide;
403. N-(4-fluorobenzyl)-3-[(1,3-thiazol-2-ylcarbonyl)amino]-1H-thieno[2,3-c]pyrazole-5-carboxamide;
404. N-(4-chlorobenzyl)-3-[(1,3-thiazol-2-ylcarbonyl)amino]-1H-thieno[2,3-c]pyrazole-5-carboxamide;
405. N-(4-methoxybenzyl)-3-[(1,3-thiazol-2-ylcarbonyl)amino]-1H-thieno[2,3-c]pyrazole-5-carboxamide;
406. N4-methylbenzyl)-3-[(1,3-thiazol-2-ylcarbonyl)amino]-1H-thieno[2,3-c]pyrazole-5-carboxamide;
407. N-(3-chlorobenzyl)-3-[(1,3-thiazol-2-ylcarbonyl)amino]-1H-thieno[2,3-c]pyrazole-5-carboxamide;
408. N-benzyl-3-{[4-(4-methylpiperazin-1-yl)benzoyl]amino}-1H-thieno[2,3-c]pyrazole-5-carboxamide;
409. N-2-fluorobenzyl)-3-{[4-(4-methylpiperazin-1-yl)benzoyl]amino}-1H-thieno[2,3-c]pyrazole-5-carboxamide;
410. N-(2-chlorobenzyl)-3-{[4-(4-methylpiperazin-1-yl)benzoyl]amino}-1H-thieno[2,3-c]pyrazole-5-carboxamide;
411. N-(2-methoxybenzyl)-3-{[4-(4-methylpiperazin-1-yl)benzoyl]amino}-1H-thieno[2,3-c]pyrazole-5 carboxamide;
412. N-(2-methylbenzyl)-3-{[4-(4-methylpiperazin-1-yl)benzoyl]amino}-1H-thieno[2,3-c]pyrazole-5-carboxamide;
413. N-(3-fluorobenzyl)-3-{[4-(4-methylpiperazin-1-yl)benzoyl]amino}-1H-thieno[2,3-c]pyrazole-5-carboxamide;
414. N-(3-methoxybenzyl)-3-{[4-(4-methylpiperazin-1-yl)benzoyl]amino}-1H-thieno[2,3-c]pyrazole-5-carboxamide;
415. N-(3-methylbenzyl)-3-{[4-(4-methylpiperazin-1-yl)benzoyl]amino}-1H-thieno[2,3-c]pyrazole-5-carboxamide;
416. N-(4-fluorobenzyl)-3-{[4-(4-methylpiperazin-1-yl)benzoyl]amino}-1H-thieno[2,3-c]pyrazole-5-carboxamide;
417. N-(4-chlorobenzyl)-3-{[4-(4-methylpiperazin-1-yl)benzoyl]amino}-1H-thieno[2,3-c]pyrazole-5-carboxamide;
418. N-(4-methoxybenzyl)-3-{[4-(4-methylpiperazin-1-yl)benzoyl]amino}-1H-thieno[2,3-c]pyrazole-5-carboxamide;
419. N-(4-methylbenzyl)-3-{[4-(4-methylpiperazin-1-yl)benzoyl]amino}-1H-thieno[2,3-c]pyrazole-5-carboxamide;
420. N-(3-chlorobenzyl)-3-{[4(4-methylpiperazin-1-yl)benzoyl]amino}-1H-thieno[2,3-c]pyrazole-5 carboxamide;
421. N-benzyl-3-[(4-morpholin-4-ylbenzoyl)amino]-1H-thieno[2,3-c]pyrazole-5-carboxamide;
422. N-2-fluorobenzyl)-3-[(4-morpholin-4-ylbenzoyl)amino]-1H-thieno[2,3-c]pyrazole-5 carboxamide;
423. N2-chlorobenzyl)-3-[(4-morpholin-4-ylbenzoyl)amino]-1H-thieno[2,3-c]pyrazole-5-carboxamide;
424. N-(2-methoxybenzyl)-3-[(4-morpholin-4-ylbenzoyl)amino]-1H-thieno[2,3-c]pyrazole-5-carboxamide;
425. N-(2-methylbenzyl)-3-[(4-morpholin-4-ylbenzoyl)amino]-1H-thieno[2,3-c]pyrazole-5-carboxamide;
426. N-(3-fluorobenzyl)-3-[(4-morpholin-4-ylbenzoyl)amino]-1H-thieno[2,3-c]pyrazole-5-carboxamide;
427. N-(3-methoxybenzyl)-3-[(4-morpholin-4-ylbenzoyl)amino]-1H-thieno[2,3-c]pyrazole-5-carboxamide;
428. N-(3-methylbenzyl)-3-[(4-morpholin-4-ylbenzoyl)amino]-1H-thieno[2,3-c]pyrazole-5-carboxamide;

429. N-(4-fluorobenzyl)-3-[(4-morpholin-4-ylbenzoyl)amino]-1H-thieno[2,3-c]pyrazole-5-carboxamide;
430. N-(4-chlorobenzyl)-3-[(4-morpholin-4-ylbenzoyl)amino]-1H-thieno[2,3-c]pyrazole-5-carboxamide;
431. N-(4-methoxybenzyl)-3-[(4-morpholin-4-ylbenzoyl)amino]-1H-thieno[2,3-c]pyrazole-5-carboxamide;
432. N-(4-methylbenzyl)-3-[(4-morpholin-4-ylbenzoyl)amino]-1H-thieno[2,3-c]pyrazole-5-carboxamide;
433. N-(3-chlorobenzyl)-3-[(4-morpholin-4-benzoyl)amino]-1H-thieno[2,3-c]pyrazole-5-carboxamide;

The invention claimed is:

1. A combinatorial chemical library comprising a plurality of members of formula (VIII)

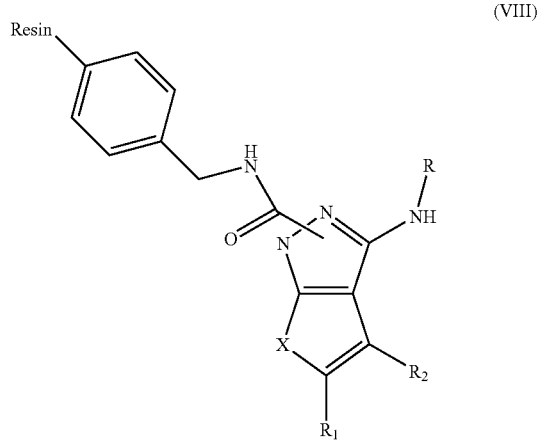

(VIII)

wherein
X is NR', O, S, SO or $SO_2$;
each of R and $R_1$, being the same or different, is independently a hydrogen atom or an optionally substituted group selected from R', —COR', —COOR', —CONHR', —CONR'R", —$SO_2$R', —$SO_2$NHR' or —$SO_2$NR'R";
wherein each of R' and R", being the same or different, is independently selected from hydrogen or an optionally further substituted straight or branched $C_1$-$C_6$ alkyl, aryl or aryl-$C_1$-$C_6$ alkyl group;
$R_2$ is an optionally substituted group selected from R', —$CH_2$OR' and OR', wherein R' is as above defined; and the pharmaceutically acceptable salts thereof.

2. The library of claim 1 wherein the resin is a polystyrenic resin.

3. A chemical library of compounds comprising two or more derivatives of formula (I)

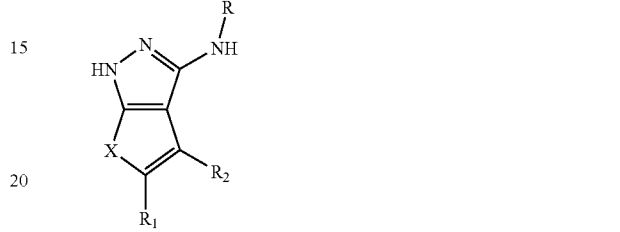

(I)

wherein
X is NR', O, S, SO or $SO_2$;
each of R and $R_1$, being the same or different, is independently a hydrogen atom or an optionally substituted group selected from R', —COR', —COOR', —CONHR', —CONR'R", —$SO_2$R', —$SO_2$NHR' or —$SO_2$NR'R";
wherein each of R' and R", being the same or different, is independently selected from hydrogen or an optionally further substituted straight or branched $C_1$-$C_6$ alkyl, aryl or aryl-$C_1$-$C_6$ alkyl group;
$R_2$ is an optionally substituted group selected from R', —$CH_2$OR' and OR', wherein R' is as above defined; and the pharmaceutically acceptable salts thereof with the proviso that such derivatives are not 4-phenyl-5-(phenylsulfonyl)-2H-thieno[2,3-c]pyrazol-3-amine or 5-phenyl-1H-furo[2,3-c]pyrazol-3-amine.

4. The polystyrenic resin according to claim 2 wherein said resin is methylisocyanate polystyrenic resin.

* * * * *